United States Patent
Yang et al.

(10) Patent No.: US 6,216,049 B1
(45) Date of Patent: Apr. 10, 2001

(54) COMPUTERIZED METHOD AND APPARATUS FOR ANALYZING NUCLEIC ACID ASSAY READINGS

(75) Inventors: Harry Yang, Rockville; Daniel L. Schwarz, Abingdon; Christopher M. Embres, Bel Air; Richard L. Moore, Catonsville, all of MD (US); Perry D. Haaland, Chapel Hill, NC (US); Paula V. Johnson, Baltimore, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/196,123

(22) Filed: Nov. 20, 1998

(51) Int. Cl.[7] .................. G05B 13/02; G06F 101/14; C12Q 1/70
(52) U.S. Cl. .................. 700/51; 702/179; 435/5
(58) Field of Search .............. 702/179; 700/51; 435/5, 6, 1–4

(56) References Cited

U.S. PATENT DOCUMENTS

| | | | |
|---|---|---|---|
| 5,526,281 | * | 6/1996 | Chapman et al. ............... 702/22 |
| 5,706,208 | * | 1/1998 | Osten et al. ............... 702/19 |
| 5,858,648 | * | 1/1999 | Steel et al. ............... 435/5 |
| 6,043,880 | * | 3/2000 | Andrews et al. ............ 356/311 |
| 6,081,766 | * | 6/2000 | Chapman et al. ............ 702/27 |
| 6,094,626 | * | 7/2000 | Kephart et al. ............ 702/179 |

FOREIGN PATENT DOCUMENTS

| | | | |
|---|---|---|---|
| 0 640 828 A1 | 3/1995 | (EP) | G01N/21/64 |
| 0 878 554 A2 | 11/1998 | (EP) | C12Q/1/68 |
| WO 95/30139 | 11/1995 | (WO) | G01N/21/64 |
| WO 96/19731 | 6/1996 | (WO) | G12Q/1/68 |
| WO 97/46714 | 12/1997 | (WO) | C12Q/1/68 |

OTHER PUBLICATIONS

Smith, Stephn W., "The Scientist and Engineer's Guide to Digital Signal Processing", California Technical Publishing, Chap 15 (1997).

Spears, P.A. et al., *Analytical Biochemistry*, 130–137, vol. 247 (1997).

* cited by examiner

Primary Examiner—William Grant
Assistant Examiner—Ronald D Hartman, Jr.
(74) Attorney, Agent, or Firm—David W. Highet

(57) ABSTRACT

A computerized method and apparatus are disclosed for analyzing numerical data pertaining to a sample assay comprising at least one biological or chemical sample. The data include a set of data pertaining to each respective sample, with each set of data including a plurality of values each representing a condition of the sample at a given time. The method and apparatus assign a respective numerical value to each of the data values, mathematically combine the numerical values to generate a total value, compare the total value to a threshold value, and control the system to indicate whether the sample has a predetermined characteristic based on a result of the comparison. Prior to calculation of the sample value, filtering, normalizing and other correcting operations can be performed on the data to correct anomalous values in the data which could adversely affect the accuracy of the results. The method and apparatus perform the described functions by representing the data values as points on a graph having a vertical axis representing the magnitudes of the values and a horizontal axis representing a period of time during which readings of the sample were taken to obtain the data values, identifying points on the graph having an anomalous characteristic, and correcting the anomalous points to produce a corrected plot of points on the graph, with each of the points of the corrected plot representing a magnitude of a corresponding one of the values. An area value is then calculated which represents an approximate area between at least a portion of the corrected plot of points on the graph and the horizontal axis. The area value is compared to a threshold value to determine whether a certain condition exists in the sample to which the set of data pertains.

18 Claims, 19 Drawing Sheets

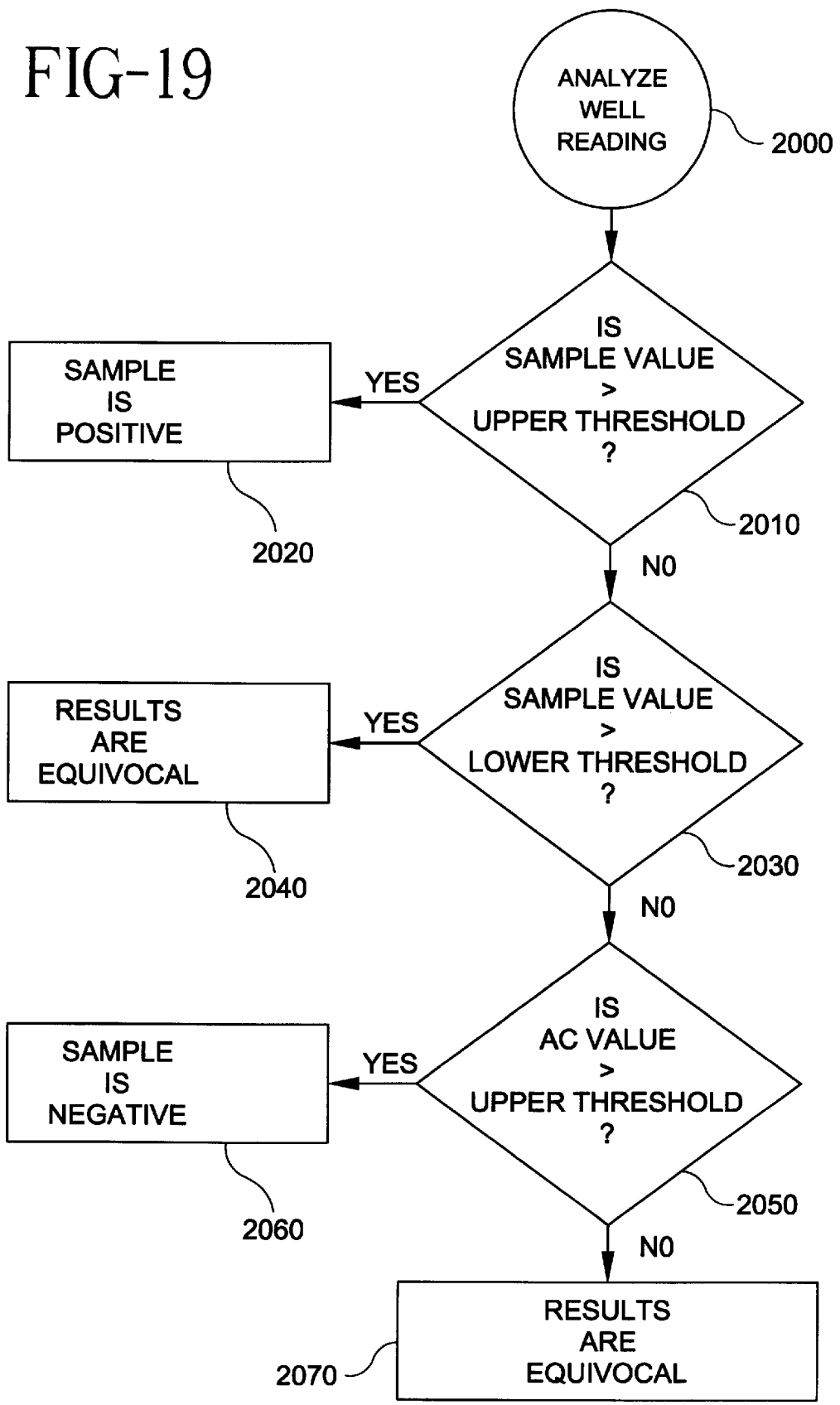

COMPUTERIZED METHOD AND APPARATUS FOR ANALYZING NUCLEIC ACID ASSAY READINGS

CROSS-REFERENCE TO RELATED APPLICATION

Related subject matter is disclosed in a copending U.S. patent application of Jeffrey P. Andrews, Christian V. O'Keefe, Brian G. Scrivens, Willard C. Pope, Timothy Hansen and Frank L. Failing entitled "Automated Optical Reader for Nucleic Acid Assays", Ser. No. 08/929,895, filed on Sep. 15, 1997, which is expressly incorporated herein by reference.

BACKGROUND OF THE INVENTION

The present invention relates generally to a computerized method and apparatus for analyzing sets of readings taken of respective samples in a biological or chemical assay, such as nucleic acid assay, to determine which samples possess a certain predetermined characteristic. More particularly, the present invention relates to a computerized method and apparatus which collects optical readings of a biological or chemical sample taken at different times during a reading period, corrects for abnormalities in the readings, and mathematically combines the values of certain of the readings to generate a sample indicator value which indicates a particular characteristic of the sample, such as the presence of a targeted pathogen in the sample.

In the clinical diagnosis of infectious disease, including sexually transmitted diseases such as Neisseria gonorrhea (GC) and chlamydia trachomatis (CT), a sample of body fluid obtained from the patient can be cultured to test for the presence of the particular organism of interest. Unfortunately, this is a relatively time-consuming process, generally requiring several days to produce a definitive result. During this time, a patient suspected of having such a disease may need to be isolated to prevent further spread of the disease.

The advent of DNA probes, which can identify specific organisms by testing for the presence of a unique DNA sequence in the sample obtained from the patient, has greatly increased the speed and reliability of clinical diagnostic testing. A test for the presence of CT or GC, for example, in a sample can be completed within several hours or less using DNA probe technology. This allows treatment to begin more quickly.

In the use of DNA probes for clinical diagnostic purposes, a nucleic acid amplification reaction is usually carried out in order to multiply the target nucleic acid into many copies or amplicons. Examples of nucleic acid amplification reactions include strand displacement amplification (SDA) and polymerase chain reaction (PCR). Detection of the nucleic acid amplicons can be carried out in several ways, most involving hybridization (binding) between the amplified target DNA and specific probes.

Many common DNA probe detection methods involve the use of fluorescein dyes. One known detection method is fluorescent energy transfer. In this method, a detector probe is labeled both with a fluorescein dye that emits light when excited by an outside source, and with a quencher which suppresses the emission of light from the flourescein dye in its native state. When DNA amplicons are present, the fluourescein-labeled probe binds to the amplicons, is extended, and allows fluorescent emission to occur. The increase of fluorescence is taken as an indication that the disease-causing organism is present in the patient sample.

Several types of optical readers or scanners exist which are capable of exciting fluid samples with light, and then detecting any light that is generated by the fluid samples in response to the excitation. For example, an X-Y plate scanning apparatus, such as the CytoFluor Series 4000 made by PerSeptive Biosystems, is capable of scanning a plurality of fluid samples stored in an array of microwells. The apparatus includes a scanning head for emitting light toward a particular sample, and for detecting light generated from the sample. During operation, the optical head is moved to a suitable position with respect to one of the sample wells. A light emitting device is activated to transmit light through the optical head toward the sample well. If the fluid sample in the well fluoresces in response to the emitted light, the fluorescent light is received by the scanning head and transmitted to an optical detector. The detected light is converted by the optical detector into an electrical signal, the magnitude of which is indicative of the intensity of the detected light. This electrical signal is processed by a computer to determine whether the target DNA is present or absent in the fluid sample based on the magnitude of the electrical signal. Each well in the microwell tray (e.g., 96 microwells total) can be read in this manner.

Another more efficient and versatile sample well reading apparatus is described in the above-referenced copending U.S. patent application, Ser. No. 08/929,895. In that system, a microwell array, such as the standard microwell array having 12 columns of eight microwells each (96 microwells total), is placed in a movable stage which is driven past a scanning bar. The scanning bar includes eight light emitting/detecting ports that are spaced from each other at a distance substantially corresponding to the distance at which the microwells in each column are spaced from each other. Hence, an entire column of sample microwells can be read with each movement of the stage.

As described in more detail below, the stage is moved back and forth over the light sensing bar, so that a plurality of readings of each sample microwell are taken at desired intervals. In one example, readings of each microwell are taken at one-minute intervals for a period of one hour. Accordingly, 60 readings of each microwell are taken during a well reading period. These readings are then used to determine which samples contain the particular targeted disease or diseases (e.g., CT and/or GC).

Several methods are known for analyzing the sample well reading data to determine whether a sample contained in the sample well includes the targeted disease or diseases. For instance, as discussed above, a nucleic acid amplification reaction will cause the target nucleic acid (e.g., CT or GC) to multiply into many amplicons. The fluorescein-labeled probe which binds to the amplicons will fluoresce when excited with light. As the number of amplicons increases over time while the nucleic acid amplification reaction progresses, the amount of fluorescence correspondingly increases. Accordingly, after a predetermined period of time has elapsed (e.g. 1 hour), the magnitude of fluorescence emission from a sample having the targeted disease (a positive sample) is much greater then the magnitude of fluorescence emission from a sample not having the targeted disease (a negative sample). In actuality, the magnitude of fluorescence of a negative sample essentially does not change throughout the duration of the test.

Therefore, the value of the last reading taken for each sample can be compared with a known threshold value, which has previously been determined. If the sample value is above the threshold value, the sample is identified as a positive sample in which the targeted disease is present.

However, if the last value taken of the sample is below the threshold value, the sample is identified as a negative sample free from the disease.

Although this "endpoint detection" method can generally be effective in identifying positive and negative samples, it is not uncommon for this method to incorrectly identify a negative sample as being positive or vice-versa The accuracy of the value of any individual sample reading can be adversely effected by factors such as a bubble forming in the sample, obstruction of excitation light and/or fluorescence emission from the sample due to the presence of debris on the optical reader, and so on. Accordingly, if the final reading of a particular sample is erroneous and only that reading is analyzed, the likelihood of obtaining a false positive or false negative result is relatively high.

Furthermore, in some instances, the magnitude of fluorescent emission from the sample decreases with the passage of time due to, for example, quenching from the patient sample, side reactions from contaminants, or destruction of the fluorescein products due to unknown effects. Accordingly, the magnitude of the last reading taken of the sample can be less than the magnitude of a reading taken at the time when the signal from the sample is at its peak. In some instances, the signal can be lower then the predetermined threshold value, in which event the positive sample is falsely identified as a negative sample.

In order to avoid these drawbacks, other methods have been developed. In one method, the overall change in the magnitudes of sample readings is calculated and compared to a known value having a magnitude indicative of a positive result. Accordingly, if the magnitude of change is greater than the predetermined value, the sample is identified as a positive sample having the targeted disease. On the other hand, if the magnitude of change is less than the predetermined value, the sample is identified as a negative sample.

Although this method may be more effective than the endpoint detection method discussed above, certain flaws in this method also exist. For example, if a sample contains a particularly large amount of target DNA, the amount of amplicons generated due to the amplification process may reach a maximum at the time the initial reading is taken, and increase very little, if at all, or even decrease, throughout the duration of the reading period. In this event, the change which occurs between the initial readings and final readings is minimal even though the sample is positive. Hence, the sample may incorrectly be identified as a negative sample.

Accordingly, a continuing need exist for a method and apparatus for analyzing data representative of readings taken of sample wells to accurately identify the samples as being positive or negative for a particular disease.

SUMMARY OF THE INVENTION

An object of the present invention is to provide a method and apparatus for accurately interpreting the values of data obtained from taking readings of a biological or chemical sample, to ascertain the presence of a particular disease in the sample based on the data values.

Another object of the invention is to provide a method and apparatus, for use with an optical sample well reader, which accurately interprets data representing magnitudes of fluorescence emissions detected from the sample at predetermined periods of time, to ascertain the presence of a particular disease in the sample.

A further object of the invention is to provide a method and apparatus for analyzing data obtained from reading a biological or chemical sample contained in a sample well, and without using complicated arithmetic computations, correcting for errors in the data which could adversely affect the results of the analysis.

These and other objects of the invention are substantially achieved by providing a computerized method and apparatus for analyzing numerical data pertaining to a sample assay comprising at least one biological or chemical sample, with the data including a set of data pertaining to each respective sample, and each set of data including a plurality of values each representing a condition of the respective sample at a point in time. The method and apparatus assign a respective numerical value to each of the data values, mathematically combine certain of the numerical values to generate a total value, compare the total value to a threshold value, and indicate whether the sample has a predetermined characteristic based on a result of the comparison. Additionally, prior to the sample value being calculated, filtering, normalizing and other correcting operations can be performed on the data to correct or remove extraneous values in the data which could adversely affect the accuracy of the results.

The method and apparatus perform all of the above functions by representing each of the plurality of data values as points on a graph having a vertical axis representing the magnitudes of the values and a horizontal axis representing a period of time during which readings of the sample were taken to obtain said plurality of data values, identifying points on the graph having an erroneous characteristic, and removing or correcting the erroneous points to produce a corrected plot of points on the graph, with each of the points of the corrected plot of points representing a magnitude of a corresponding one of the values. An area value is then calculated which represents an approximate area between a portion of the corrected plot of points on the graph and the horizontal axis, and the area value is compared to a threshold value to determine whether a certain condition exists in the sample to which the set of data pertains.

BRIEF DESCRIPTION OF THE DRAWINGS

These and other objects of the invention will be more readily appreciated from the following detailed description when read in conjunction with the accompanying drawings, in which:

FIG. 19 is a flowchart showing the steps performed for analyzing well readings based on the value of the area calculated in the area calculating steps shown in the flowchart of FIG. 18.

DETAILED DESCRIPTION OF THE PREFERRED EMBODIMENTS

Figure 1:
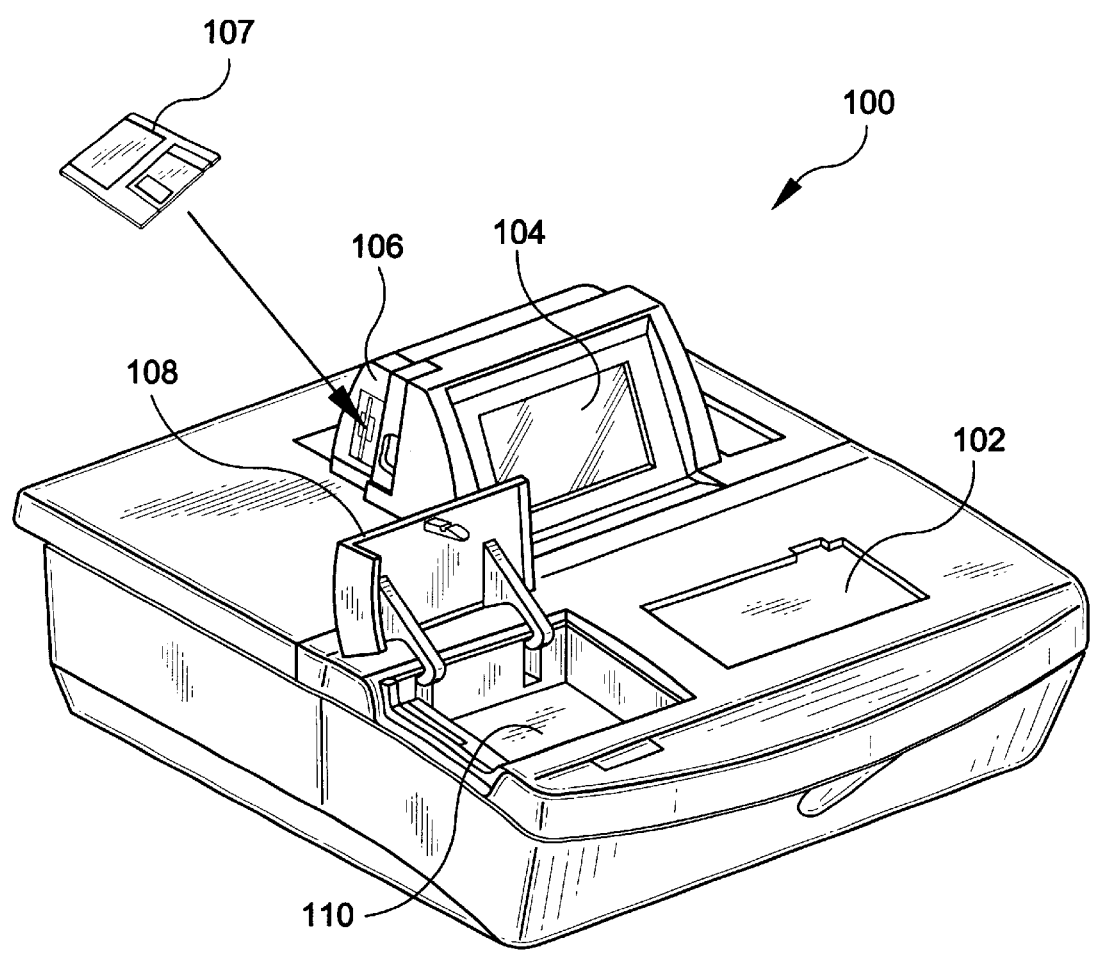
FIG. 1 is schematic view of an apparatus for optically reading sample wells in a sample well array, which employs an embodiment of the present invention to interpret the sample well readings.

A well reading apparatus 100 according to an embodiment of the present invention is shown in FIG. 1. The apparatus 100 includes a keypad 102, which enables an operator to enter data and thus control operation of the apparatus 100. The apparatus 100 further includes a display screen 104, such as an LCD display screen or the like, for displaying "soft keys" which allow the operator to enter data and control operation of the apparatus 100, and for displaying information in response to the operator's commands, as well as data pertaining to the scanning information gathered from the samples in the manner described below. The apparatus also includes a disk drive 106 into which can be inserted a floppy disk 107 for storing data generated by the apparatus 100, or from which the apparatus can read data or control programs.

Figure 2:
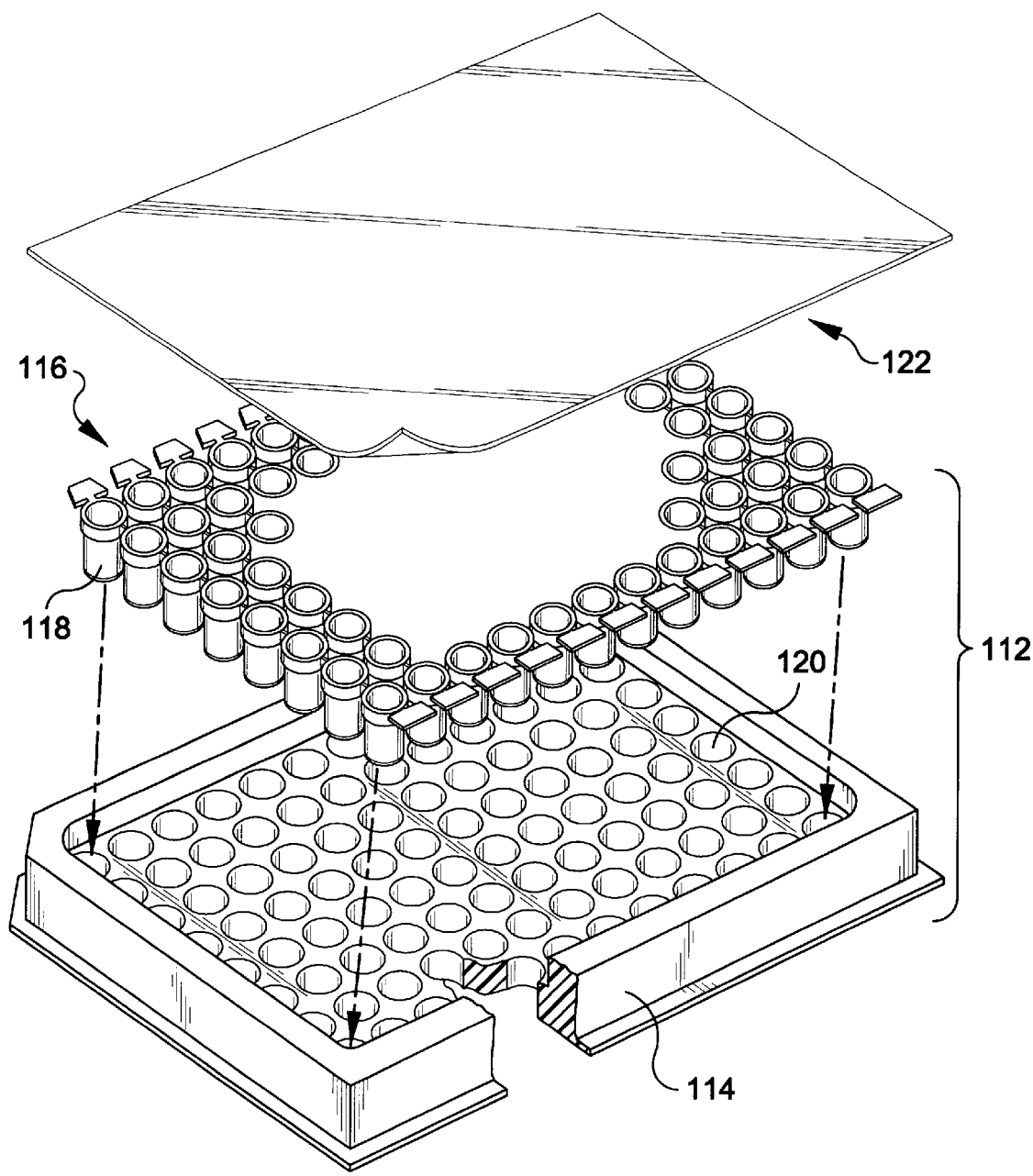
FIG. 2 is an exploded perspective view of a sample well tray for use in the sample well reading apparatus shown in FIG. 1.

The apparatus 100 further includes a door 108 which allows access to a stage assembly 110 into which can be loaded a sample tray assembly 112. As shown in FIG. 2, a sample tray assembly 112 includes a tray 114 into which is loaded a microwell array 116, which can be a standard microwell array having 96 individual microwells 118 arranged in 12 columns of 8 microwells each. The tray 114 has openings 120 which pass entirely through the tray and are arranged in 12 columns of eight microwells each, such that each opening 120 accommodates a microwell 118 of microwell array 116. After the samples have been placed into the microwells 118, a cover 122 can be secured over microwells 118 to retain each fluid sample in its respective microwell 118. Further details of the sample tray assembly 112 and of sample collection techniques are described in the aforementioned copending U.S. patent application Ser. No. 08/929,895.

Each microwell can include one or more type of detector probe, as described above, for identifying a particular disease (e.g., GC or CT). If the microwell array 116 is to be used to test for both GC and CT in each patient sample, the microwells 118 are arranged in groups of three microwells each, with one microwell in the group containing a reagent which is used to identify the presence of GC, another microwell in the group a reagent which is used to identify the presence of CT, and the third microwell containing an amplification control reagent AC, the purpose of which is described in more detail below. A fluid sample from a particular patient is placed in all three wells of a particular group of wells.

Additionally, some of the 96 microwells 118 in the microwell array 116 can be designated as control sample wells for a particular disease, such as CT, with one of the control sample wells containing a control positive sample and the other control well containing a control negative sample, the purpose of which is described in detail below. Additional microwells 118 can be designated as control sample wells for GC, with one of the control sample wells including a positive sample and the other including a negative sample.

Figure 3:
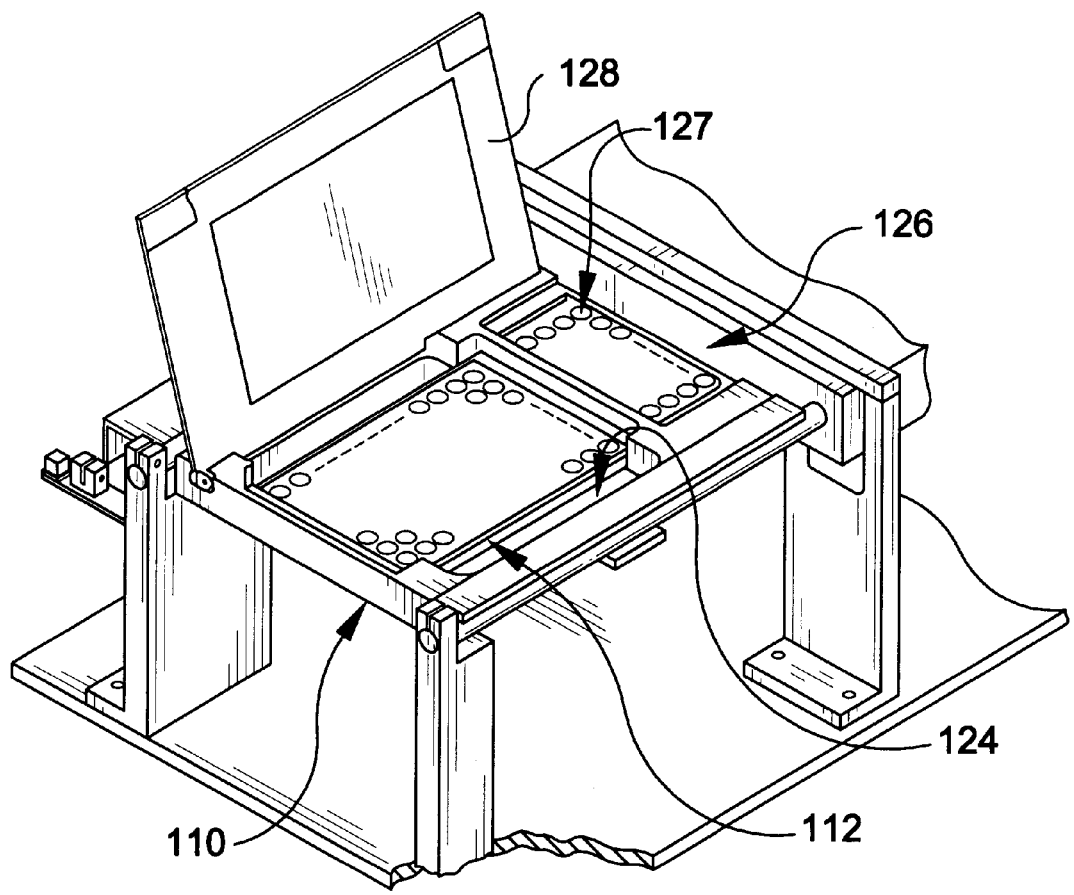
FIG. 3 is a detailed perspective view of a stage assembly employed in the apparatus shown in FIG. 1 for receiving and conveying the sample well tray assembly shown in FIG. 2.

After the patient fluid samples have been placed into the appropriate microwells 118 of the microwell array 116 in sample tray assembly 112, the sample tray assembly 112 is loaded into the stage assembly 110 of the well reading apparatus 100. The stage assembly 110, shown in more detail in FIG. 3, includes an opening 124 for receiving a sample tray assembly 112. The stage assembly 110 further includes a plurality of control wells 126 which are used in calibrating and verifying the integrity of the reading components of the well reading apparatus 100. Among these control wells 126 is a column of eight normalization wells 127, the purpose of which is described in more detail below. The stage assembly 110 further includes a cover 128 which covers the sample tray assembly 112 and control wells 126 when the sample tray assembly 112 has been loaded into the opening 124 and sample reading is to begin. Further details of the stage assembly 110 are described in the above-referenced copending U.S. patent application Ser. No. 08/929,895.

Figure 4:
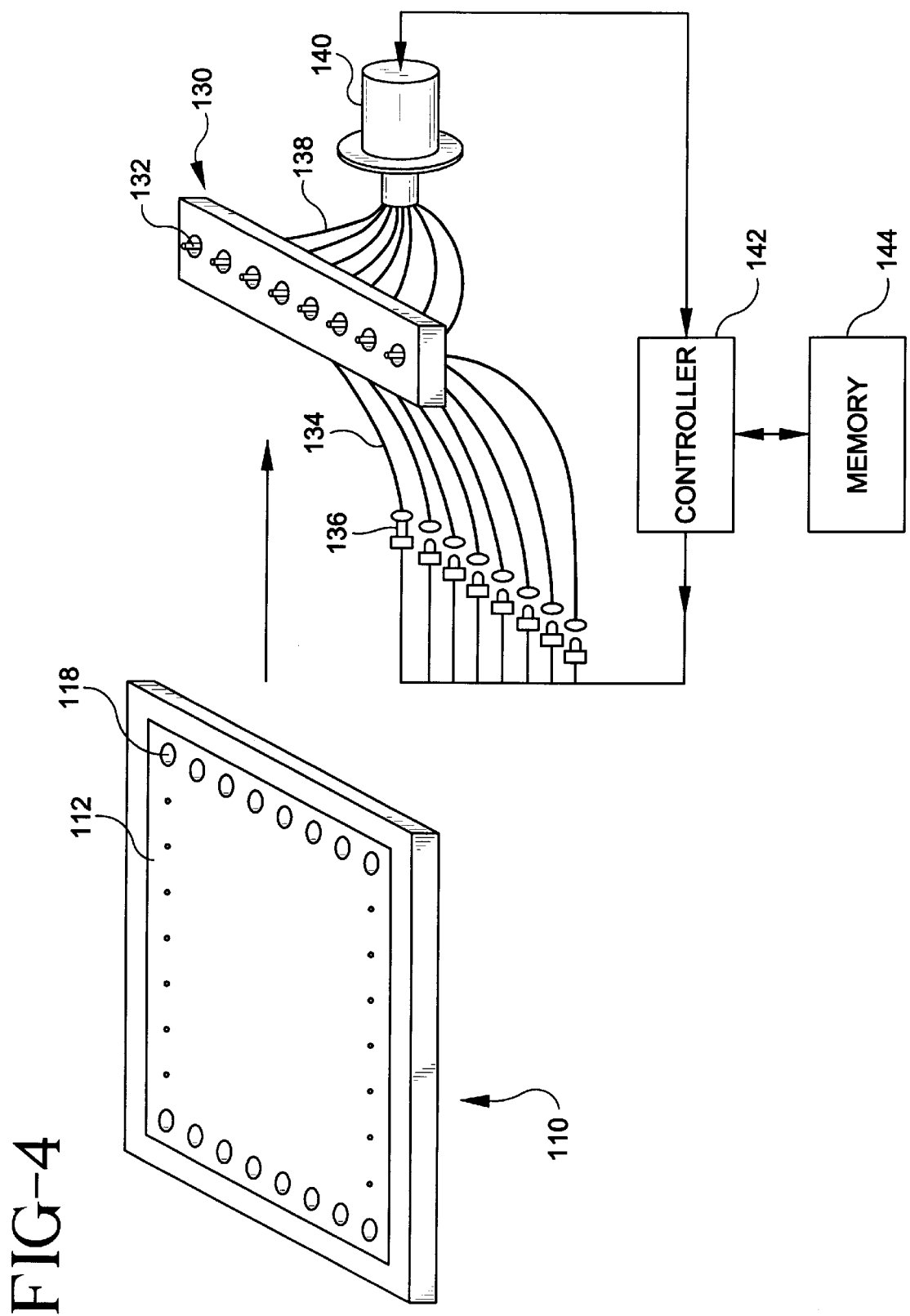
FIG. 4 is a diagram illustrating the layout of a light sensor bar and corresponding fiber optic cables, light emitting diodes and light detector employed in the apparatus shown in FIG. 1, in relation to a sample well tray being conveyed past the light sensor bar by the stage assembly shown in FIG. 3.

To read the samples contained in the microwells 118 of a sample tray assembly 112 that has been loaded into the stage assembly 110, the stage assembly 110 is conveyed past a light sensing bar 130 as shown in FIG. 4. The light sensor bar 130 includes a plurality of light emitting/detecting ports 132. The light emitting/detecting ports 132 are controlled to emit light toward a column of 8 microwells 118 when the stage assembly 110 positions the microwells 118 over the light emitting/detecting ports, and to detect fluorescent light emitted from the samples contained in the microwells 118. In this example, the light sensor bar 130 includes 8 light emitting/detecting ports 132 which are arranged to substantially align with the 8 microwells 118 in a column of the microwell array 116 when the column of microwells 118 is positioned over the light emitting/detecting ports 132.

The light emitting/detecting ports 132 are coupled by respective fiber optic cables 134 to respective light emitting devices 136, such as LEDs or the like. The light emitting/detecting ports 132 are further coupled by respective fiber optic cables 138 to an optical detector 140, such as a photomultiplier tube or the like. The light emitting devices 136 and optical detector 140 are controlled by a controller 142 in accordance with software commands stored, for example, in a memory 144. Further details of the light sensor bar 130 and related components, as well as the manner in which the stage assembly 110 is conveyed past the light sensor bar 130 for reading the samples contained in the microwells 118, are described in the above-referenced copending U.S. patent application Ser. No. 08/929,895.

In general, one reading for each microwell is taken at a particular interval in time, and additional readings of each microwell are taken at respective intervals in time for a predetermined duration of time. In the present example, one microwell reading is obtained for each microwell 118 at approximately one-minute intervals for a period of one hour. One reading of each of the normalization wells 127, as well as one "dark" reading for each of the light emitting/detecting ports 132, is taken at each one-minute interval. Accordingly, 60 microwell readings of each microwell 118, as well as 60 readings of each normalization well 127 and 60 dark readings, are obtained during the one-hour period. As discussed above, a reading is a measurement of the intensity of the fluorescent emission being generated by a microwell sample in response to excitation light emitted toward the sample. These intensity values are stored in magnitudes of relative fluorescent units (RFUs). A reading of a sample having a high magnitude of fluorescent emission will provide an RFU value higher than that provided by a reading taken of a sample having low fluorescent emission.

Once the total number of readings (e.g. 60 readings) for each sample well have been taken, the readings for each sample must be interpreted by the well reading apparatus 100 so the well reading apparatus 100 can indicate whether the sample has tested positive or negative for a particular disease (e.g., CT or GC). The microprocessing unit of the well reading apparatus 100 is controlled by software to perform various operations on the data representing the sample well readings. The operations being described are applied in essentially the same manner to the readings taken for each sample microwell 118. Accordingly, for illustrative purposes, the operations will be described with regard to readings taken for one sample microwell 118, which will be referred to as the first sample microwell 118.

As discussed above, during each one-minute interval in which all of the microwells 118 in the sample tray assembly 112 are read, the light sensor bar 130 reads the normalization wells one time. Hence, after 60 readings of each microwell sample have been taken, each normalization well 127 has been read 60 times by its respective light emitting/detecting port 132 of the light sensor bar 130, which results in eight sets of 60 normalization well readings. For illustrative purposes, the normalization readings of the normalization well 127 that has been read by the light emitting/detecting port 132, which has also read the first sample microwell 118 now being discussed, are represented as $n_1$ through $n_{60}$.

Additionally, as discussed above, during each one-minute interval, the optical detector 140 is controlled to obtain a "dark" reading in which a reading is taken without any of the light emitting devices 136 being activated. This allows the optical detector 140 to detect any ambient light electronic offsets artifacts that may be present in the system. Accordingly, after 60 readings of every microwell 118 have been obtained, 60 dark readings have been obtained. For illustrative purposes, the dark readings obtained by the light emitting/detecting port 132 which read the first sample microwell 118 now being discussed are represented as $d_1$ through $d_{60}$.

Figure 5:
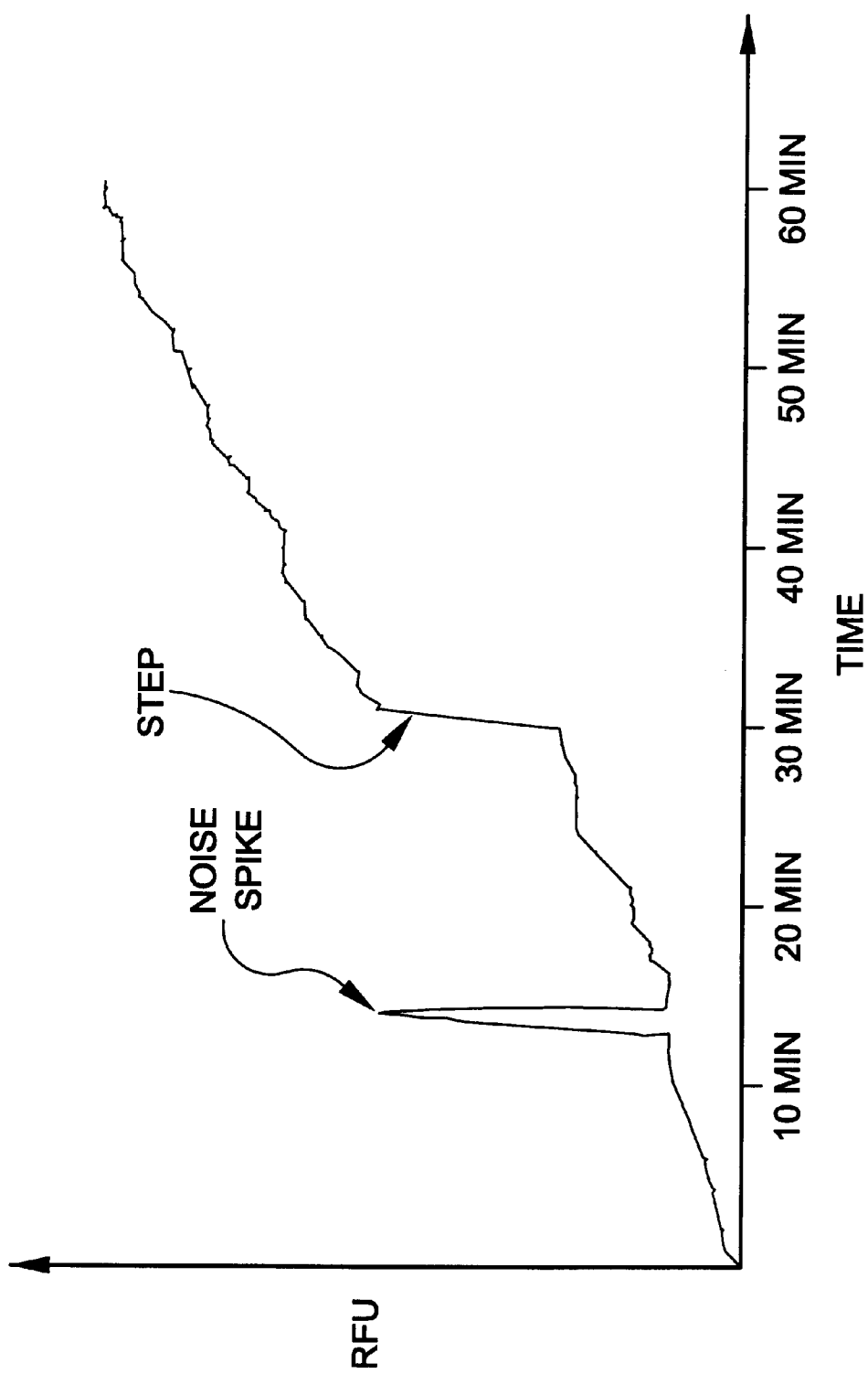
FIG. 5 is a graph illustrating values representing the magnitudes of fluorescent emissions detected from a sample well of the sample well tray shown in FIG. 2 by the apparatus shown in FIG. 1, with the values being plotted as a function of the times at which their corresponding fluorescent emissions were detected.

FIG. 5 is a graph showing an exemplary relationship of the 60 readings for one well which have been obtained during the one-hour reading period. For illustrative purposes, these readings are represented as $r_1$ through $r_{60}$. These readings are plotted on the graph of FIG. 5 with their RFU value being represented on the vertical axis with respect to the time in minutes at which the readings were taken during the reading period.

As can be appreciated from the graph, the RFU values for the readings taken later in the reading period are typically greater than the RFU values of the readings taken at the beginning of the reading. For illustrative purposes, this example shows an exemplary trend in readings for a well that contains the particular disease (e.g., CT or GC) for which the well is being tested.

As can also be appreciated from FIG. 5, the graph of the "raw data" readings include a noise spike and a step as shown. The process that will now be described eliminates noise spikes, steps or other apparent abnormalities in the graph which are typically the result of erroneous readings being taken of the sample well.

Figure 6:
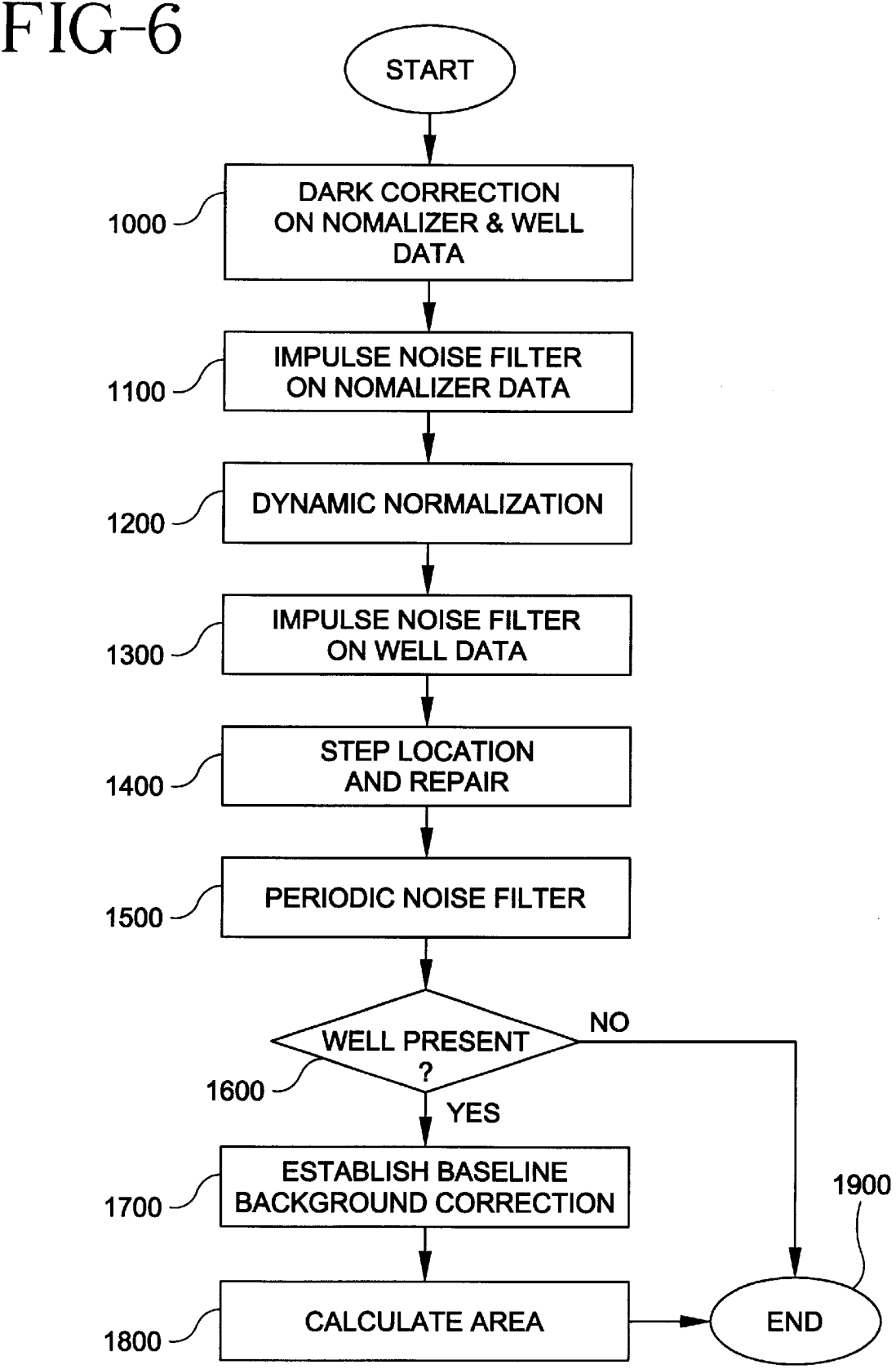
FIG. 6 is a flowchart showing the steps of a method for normalizing, filtering, adjusting and interpreting the data in the graph shown in FIG. 5 according to an embodiment of the present invention.

The flowchart shown in FIG. 6 represents the overall process for interpreting the graph of raw data readings $r_1$ through $r_{60}$ shown in FIG. 5 to provide a well sample result which is used to determine whether the well sample includes the particular target disease for which it is being tested. These processes are performed by the controller 142 of the well reading apparatus 100 as controlled by software, which can be stored in a memory 144 resident in the well reading apparatus 100, or on a disk 107 inserted into disk drive 106.

As shown in FIG. 6, the software initially controls the controller to perform a dark correction on the normalizer data readings $n_1$ through $n_{60}$ and on the well readings $r_1$ through $r_{60}$. The details of this step are shown in the flowchart of FIG. 7 and in step 1 of the pseudo-code set forth in the attached Appendix.

Figure 7:
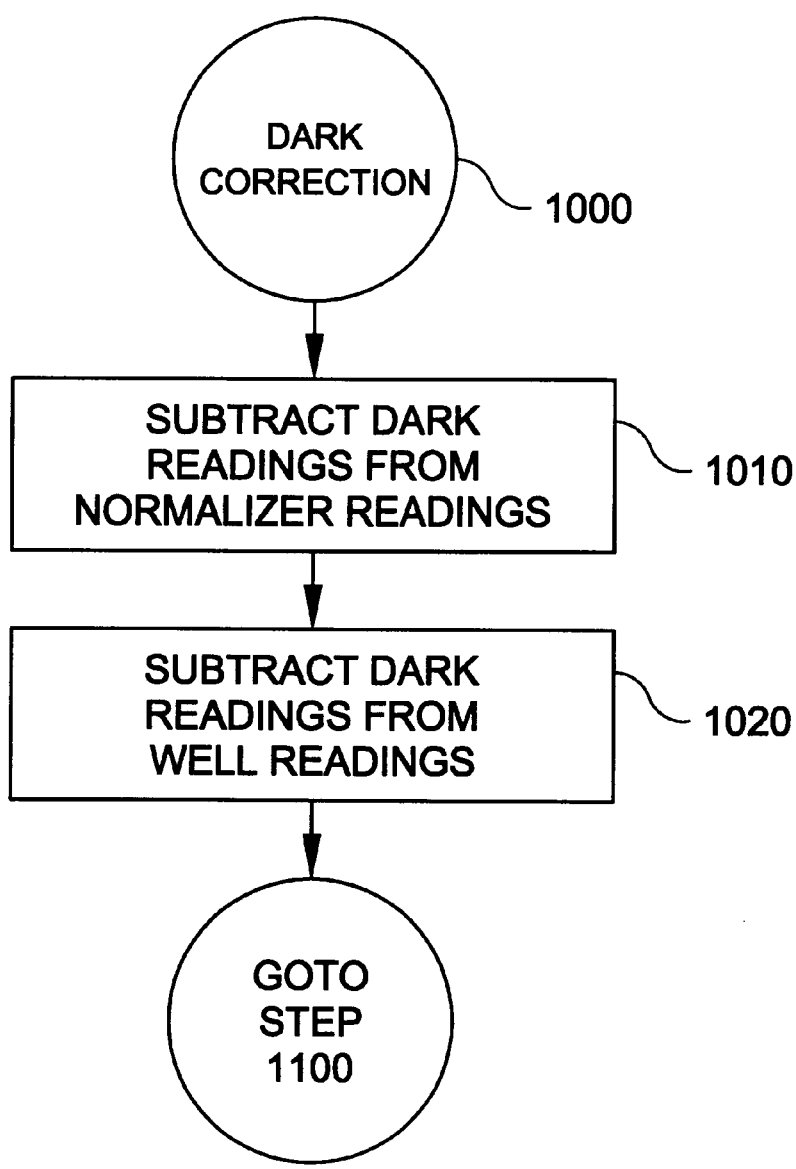
FIG. 7 is a flowchart showing the steps of the dark correction processing step of the flowchart shown in FIG. 6.

In particular, in step 1010 of FIG. 7, the dark reading values $d_1$ through $d_{60}$ are subtracted from the corresponding normalizer reading values $n_1$ through $n_{60}$, respectively, to provide corrected normalizer readings $cn_1$ through $cn_{60}$, respectively. That is, dark reading $d_1$ is subtracted from normalizer reading $n_1$ to provide corrected normalizer reading $cn_1$, dark reading $d_2$ is subtracted from normalizer reading $n_2$ to provide corrected normalizer reading $cn_2$, and so on.

The processing then proceeds to step 1020 in which the dark readings $d_1$ through $d_{60}$ are subtracted from their corresponding well readings $r_1$ through $r_{60}$, respectively, to provide corrected well readings $c_1$ through $c_{60}$, respectively. That is, dark well reading $d_1$ is subtracted from well reading $r_1$ to provide corrected well reading $c_1$, dark reading $d_2$ is subtracted from well reading $r_2$ to provide corrected well reading $cr_2$, and so on.

Figure 8:
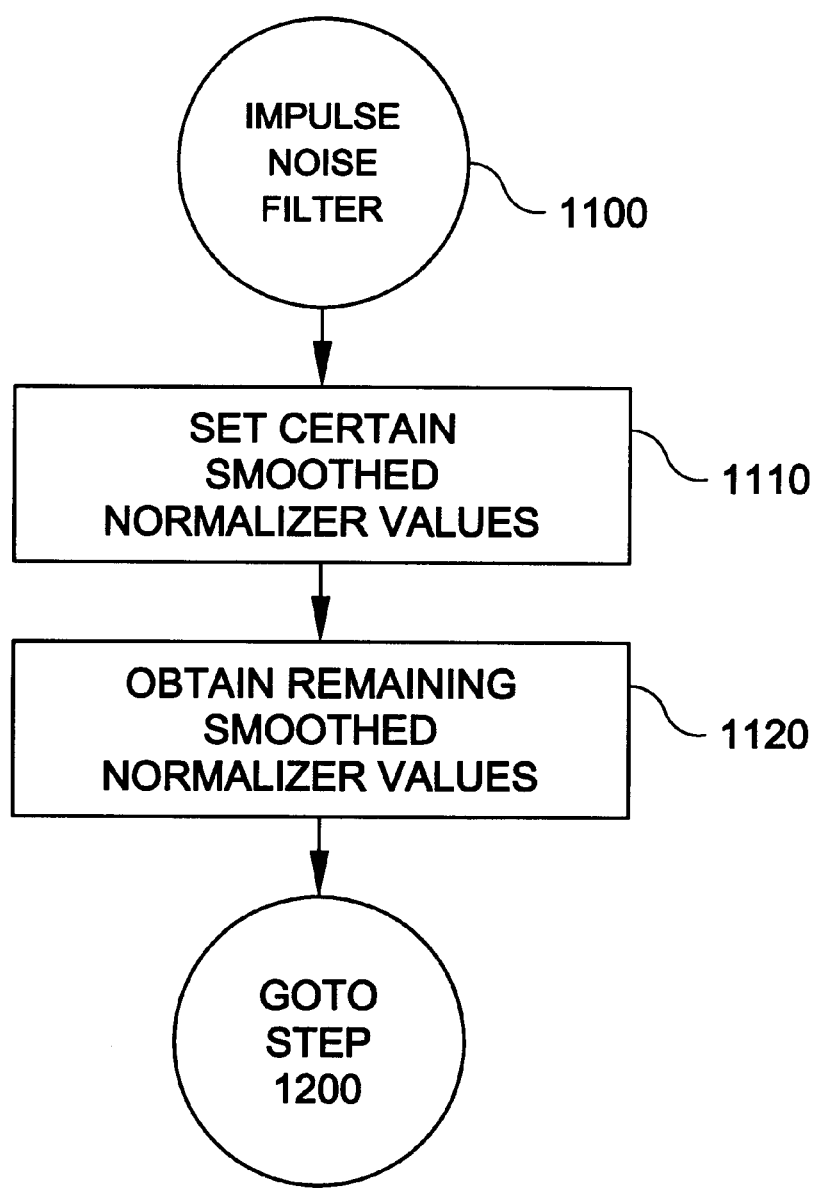
FIG. 8 is a flowchart showing the steps of the impulse noise filter on normalizer data processing step of the flowchart shown in FIG. 6.

After all of the corrected normalizer readings and corrected well readings have been obtained, the processing continues to the filtering operation in step 1100 of the flowchart shown in FIG. 6, in which noise is filtered from the corrected normalizer readings $cn_1$ through $cn_{60}$ which were obtained during step 1010 described above. Details of step 1100 are shown in FIG. 8, and in step 2 in the attached pseudo-code. Specifically, in this example, a five-point running median is applied to the corrected normalizer readings $cr_1$ through $cr_{60}$.

As shown in step 1110 of FIG. 8, the first two smoothed normalizer values $xn_1$ and $xn_2$ are set equal to the first two corrected normalizer values $cn_1$ and $cn_2$, respectively, while the last two smoothed normalizer values $xn_{59}$ and $xn_{60}$ are set equal to the last two corrected normalizer values $cn_{59}$ and $cn_{60}$. Then, in step 1120, smoothed normalizer values $xn_3$ through $xn_{58}$ are obtained as median value of their corresponding corrected normalizer values $cn_3$ through $cn_{58}$, respectively, and surrounding corrected normalizer values. For example, smoothed nonnalizer value $xn_3$ is set equal to median value of corrected normalizer values $cn_1$, $cn_2$, $cn_3$, $cn_4$, and $cn_5$. Similarly, the smoothed normalizer value $xn_4$ is set equal to median value of corrected normalizer values $cn_2$, $cn_3$, $cn_4$, $cn_5$, and $cn_6$, and smoothed normalizer values $xn_5$ through $xn_{58}$ are calculated in a similar manner.

Figure 9:
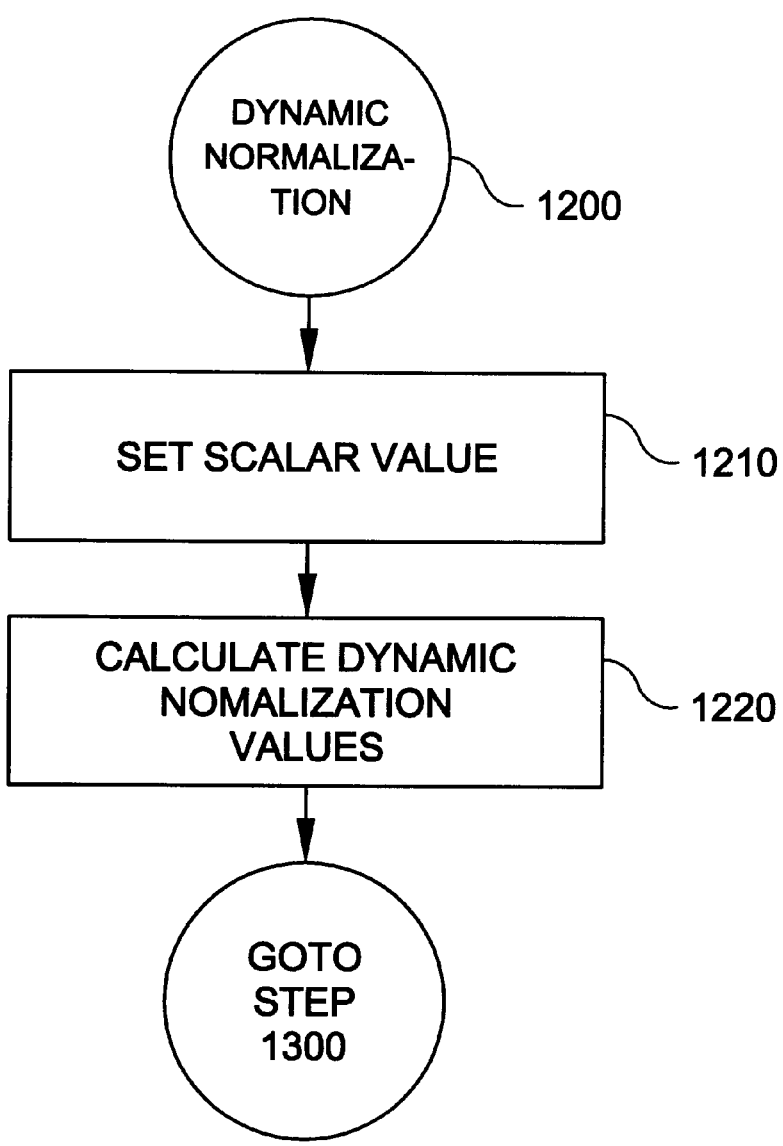
FIG. 9 is a flowchart showing the steps of the dynamic normalization processing step of the flowchart show in FIG. 6.

Once all smoothed normalizer values $xn_1$ through $xn_{60}$ have been obtained, the processing continues to the dynamic normalization step 1200 shown in the flowchart of FIG. 6. The details of the dynamic normalization process are shown in the flowchart of FIG. 9, as well as in step 3 of the attached psuedo-code. Specifically in this example, the smoothed normalizer values $xn_1$ through $xn_{60}$, as well as the corrected well reading values $cr_1$ through $cr_{60}$, are used to calculate dynamic normalization values $nr_1$ through $nr_{60}$.

In step 1210, a scalar value is set which is used to control the magnitude of the values used in the calculations. In this example, the scalar value is 3000, but it can be any suitable value. The processing then proceeds to step 1220, where the scalar value, corrected well reading values, and smoothed normalizer values are used to calculate dynamic normalization values. In particular, to calculate the dynamic normalization values, the corresponding corrected well value is multiplied by the scalar value, and then that total is divided by the corresponding smoothed normalizer value. For instance, to obtain dynamic normalization value $nr_1$, corrected well reading value $cr_1$ is multiplied by 3000 (the scalar value), and then that total is divided by the value of smoothed normalizer value $xn_1$. Similarly, dynamic normalization value $nr_2$ is calculated by multiplying corrected well reading value $cr_2$ by 3000, and then dividing that total by smoothed normalizer value $xn_2$. This process continues until all 60 dynamic normalization values $nr_1$ through $nr_{60}$ have been obtained.

Figure 10:
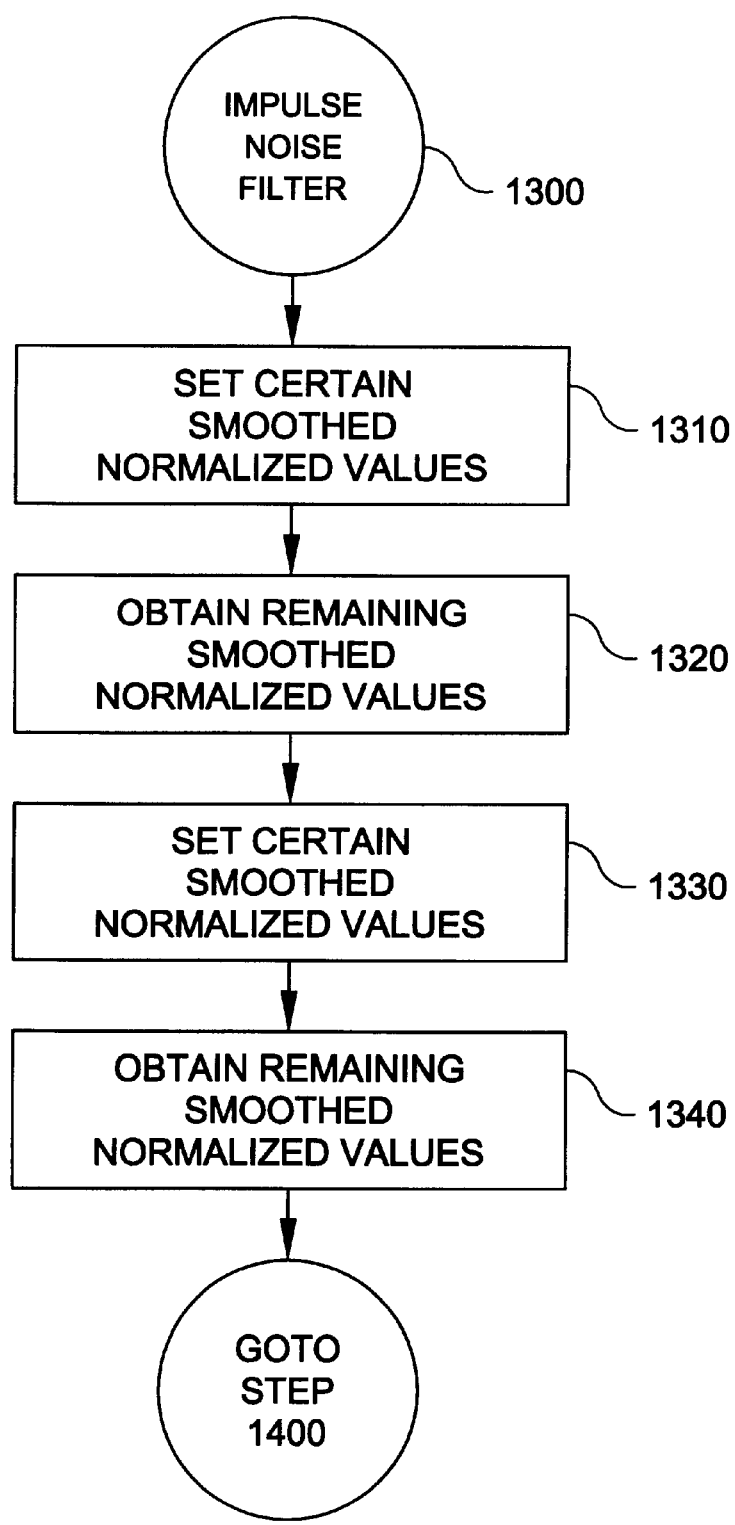
FIG. 10 is a flowchart showing the steps of the impulse noise filter on well data processing step of the flowchart shown in FIG. 6.

The processing then continues to perform the input noise filtering operation on the well data as shown in step 1300 of the flowchart in FIG. 6. The details of this operation are shown in the flowchart of FIG. 10, as well as in step 4 of the attached psuedo-code. In step 1300, a three-point running median is applied to the dynamic normalization values $nr_1$ through $nr_{60}$ to obtain smoothed normalized values $x_1$ through $x_{60}$. To perform this operation, as shown in step 1310 of FIG. 10, the first smoothed normalized value $x_1$ is set equal to the first dynamic normalization value $nr_1$, and the last smoothed normalized value $x_{60}$ is set equal to the last dynamic normalization value in $nr_{60}$. The processing then proceeds to step 1320, where the smoothed normalized values $x_2$ through $x_{59}$ are obtained. These values are obtained by applying a three-point running median to the dynamic normalization values, such that the smoothed normalized values $x_2$ through $x_{59}$ are obtained by calculating the median of their corresponding dynamic normalization values $nr_2$ through $nr_{59}$, respectively, and the surrounding normalization values.

That is, in this example, smoothed normalized value $x_2$ is obtained by taking the median of dynamic normalization values $nr_1$, $nr_2$, and $nr_3$. Similarly, smoothed normalized value $x_3$ is obtained by taking the median of dynamic normalized value $nr_2$, $nr_3$, and $nr_4$. Smoothed normalized values $x_4$ through $x_{59}$ are obtained in a similar manner.

Once the smoothed normalized values $x_1$ through $x_{60}$ have been obtained, a three-point running median is applied to those values to obtain smoothed normalized values $z_1$ through $z_{60}$. That is, in step 1330, smoothed normalized value $z_1$ is set equal to smoothed normalized value $x_1$, and smoothed normalized value $z_{60}$ is set equal to smoothed normalized value $x_{60}$. Then, in step 1340, smoothed normalized values $z_2$ through $z_{59}$ are obtained by calculating the median of their corresponding smoothed normalized value $x_2$ through $x_{59}$ and the surrounding smoothed normalized values. That is, smoothed normalized value $z_2$ is obtained by calculating the median of smoothed normalized values $x_1$, $x_2$, and $x_3$. Similarly, smoothed normalized value $z_3$ is obtained by calculating the median of smoothed normalized values $x_2$, $x_3$, and $x_4$. Smoothed normalized value $z_4$ through $z_{59}$ are then obtained in a similar manner.

After steps 1000 through 1300 of the flowchart in FIG. 6 have been performed as described above, the well readings have been smoothened and normalized, and are represented by the smoothed normalized values $z_1$ through $z_{50}$. Accordingly, as shown in the graph of FIG. 11, when the smoothed normalized values $z_1$ through $z_{60}$ are plotted with respect to a corresponding time periods in which their corresponding well readings have been obtained, the noise spike in the graph of FIG. 5 has been eliminated.

Figure 11:
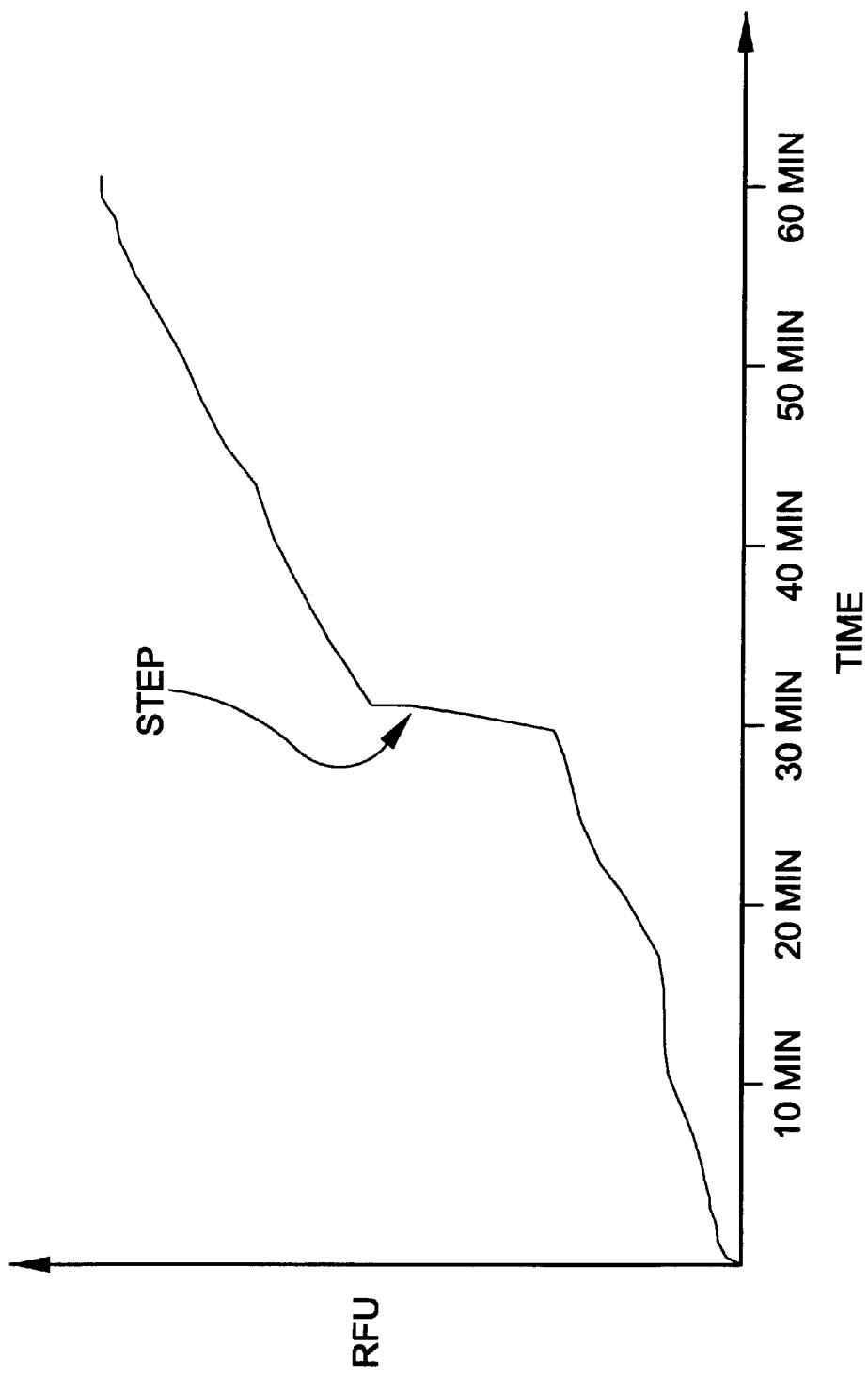
FIG. 11 is a graph which results after performing the dark correction, impulse noise filter, and dynamic normalization steps in the flowchart shown in FIGS. 6–10 on the graph shown in FIG. 5.

However, these smoothing and normalizing operation did not remove the step which is still present in the graph shown in FIG. 11. The abrupt increase in the reading values, which resulted in the step appearing in the graph, was likely caused by the presence of a bubble in the well which formed, dissipated, or moved after the $30^{th}$ well reading was obtained (i.e., after an elapsed time of 30 minutes), but before the $31^{st}$ well reading was obtained. Accordingly, the magnitudes of well reading values $r_{31}$ through $r_{60}$ and hence, and magnitudes of smoothed and normalized values $z_{31}$ through $z_{60}$, have been increased due to the presence or absence of this bubble. Therefore, it is necessary to reduce or increase the smoothed normalized values $z_{31}$ through $z_{60}$ by a value proportionate to the size of the step.

The step removal operation is performed in step 1400 as shown in the flowchart in FIG. 6. Details of the step removal operation are set forth in the flowchart in FIG. 12, and in step 5 of the attached pseudo-code.

It has been determined that graphs of these types generally will have only one or possibly two steps, and will almost never have more than five steps. Accordingly, all of the steps in the graph will likely have been located and removed after performing the step locating process five times. Accordingly, in step 1405 in the flowchart of FIG. 12, a count value is set to allow the process to repeat a maximum of five times. The process then proceeds to step 1410, where difference values $dr_1$ through $dr_{59}$ are calculated which represent the differences between adjacent smoothed normalized value $z_1$ through $z_{60}$. That is, the first difference value $dr_1$ is calculated as the value of smoothed normalized value $z_2$ minus smoothed normalized value $z_1$. The second difference value $dr_2$ is calculated as the value of smoothed normalized value $z_3$ minus smoothed normalized value $z_2$. This process is repeated until 59 difference values $dr_1$ through $dr_{59}$ have been obtained.

The processing then continues to step 1415, in which the difference values $dr_1$ through $dr_{59}$ are added together to provide an average total, which is then divided by 59 to provide a difference average 'dr. The processing then continues to step 1420, where a variance value var(dr) is calculated. This variance value is calculated by subtracting the difference value 'dr from each difference value $dr_1$ through $dr_{59}$, squaring each subtraction value, and then summing the totals of the squared values. For example, the difference value 'dr is subtracted from the first difference value $dr_1$ to provide a total, which is then squared. The difference value 'dr is then subtracted from the second difference value $dr_2$, and that total is squared. This process continues for all remaining difference values $dr_3$ through $dr_{59}$. The 59 squared totals are then added and divided by 58 to obtain the variance value (dr).

The process then continues to step 1425 where a sum value s is calculated. This sum value is calculated by subtracting the difference value dr from each of the difference values $dr_1$ through $dr_{59}$, taking each result to the fourth power to obtain a set of 59 results, and then adding all of the 59 results. That is, the difference value 'dr is subtracted from the first difference value $dr_1$ to provide a result. That result is then taken to the fourth power to provide a first result. The difference value 'dr is subtracted from second difference value $dr_2$, and the result of the subtraction is taken to the fourth power to provide a second result. This process is repeated for the remaining difference values $dr_3$ through $dr_{59}$ until all 59 results have been calculated. The 59 results are then added to provide the sum value s.

Figure 12:
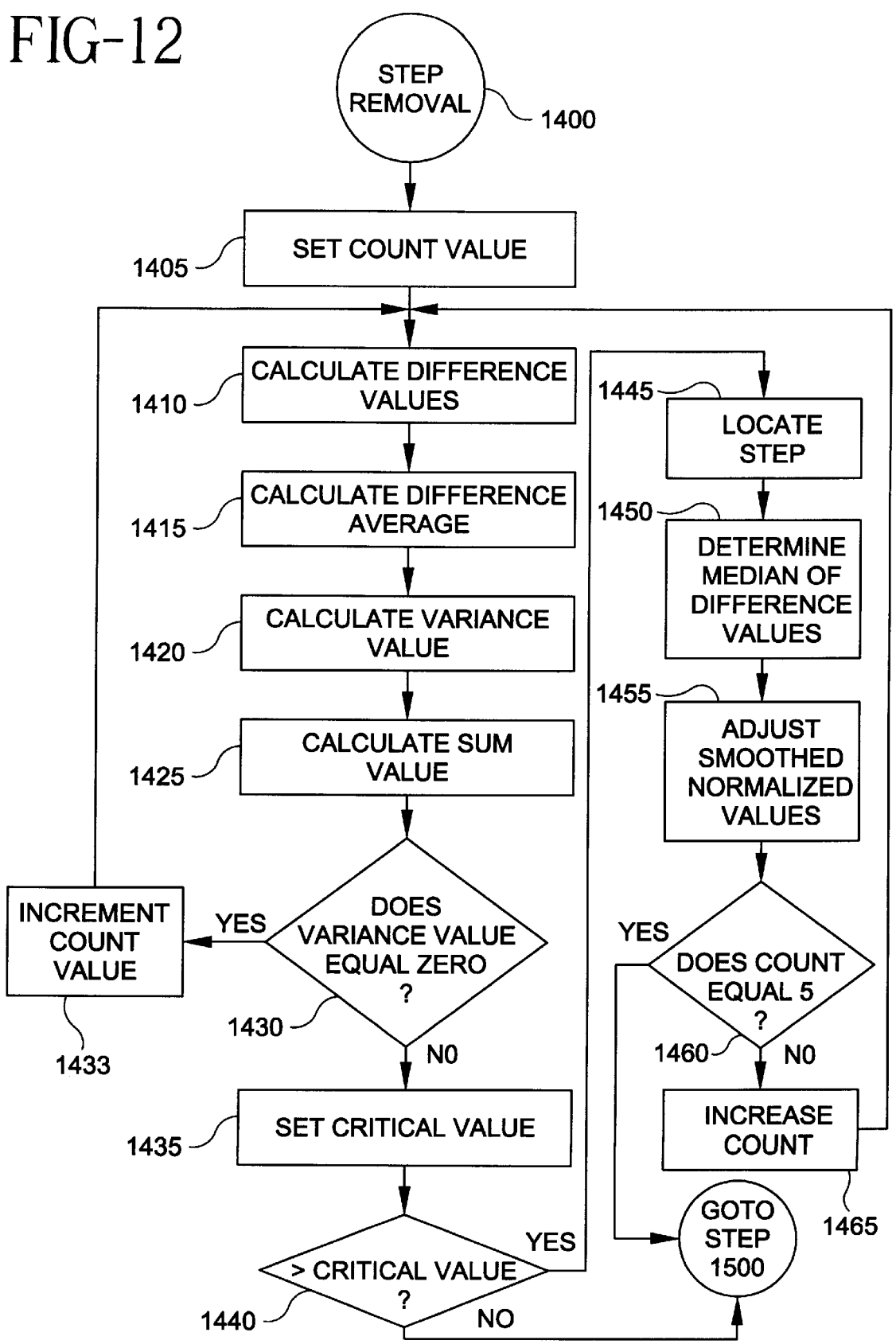
FIG. 12 is a flowchart showing steps of the step location and removal processing step of the flowchart shown in FIG. 6.

In step 1430 of FIG. 12, the processing determines whether the variance value var(dr) is equal to zero. If the value of var(dr) is equal to zero, the processing proceeds to step 1433, where the count value is incremented by one, and steps 1410 through 1425 are repeated as discussed above. However, if the value of var(dr) is not equal to zero, then the processing proceeds to step 1435. In step 1435, as critical value CRIT_VAL is set equal to 4.9. The processing then proceeds to step 1440, where it is determined whether the value of sum s divided by the total of var(d) squared multiplied by 59 is greater than the value of CRIT_VAL. If the calculated value is not greater than CRIT_VAL, then the step location and repair processing is completed, and the processing continues to the periodic noise filter processing in step 1500 shown in the flowchart of FIG. 6.

However, if the total is greater than the value of CRIT_VAL, then the processing proceeds to step 1445, where processing is performed to determine the location of the step. This is accomplished by subtracting the difference value 'dr from each of the 1 through 59 difference values $dr_1$ through $dr_{59}$, taking the absolute value of each of the subtraction results, and determining which of the absolute values is the greatest. For example, the processing first subtracts the value 'dr from the first difference value $dr_1$, and takes the absolute value of that result. This absolute value is compared with a variable max, which has initially been set to zero. If the absolute value is greater, the variable max is set to that absolute value, and the variable maxpt_dr is set equal to the number of the difference value, which in this case is 1.

The processing then subtracts difference value 'dr from the second difference value $dr_2$, and takes the absolute value of that subtraction value. The processing determines whether that absolute value is greater than the new max value. If the absolute value is greater, then max is set to that absolute value, and maxpt_dr is set equal to 2. This process is repeated for all remaining difference values $dr_3$ through $dr_{59}$. After the process is completed, maxpt_dr will be set equal to the number of the smoothed normalized value at which the largest step has occurred. As discussed above, in this example, it is presumed that the step occurred at value $z_{30}$. Accordingly, maxpt_dr is set to 30.

Figure 13:
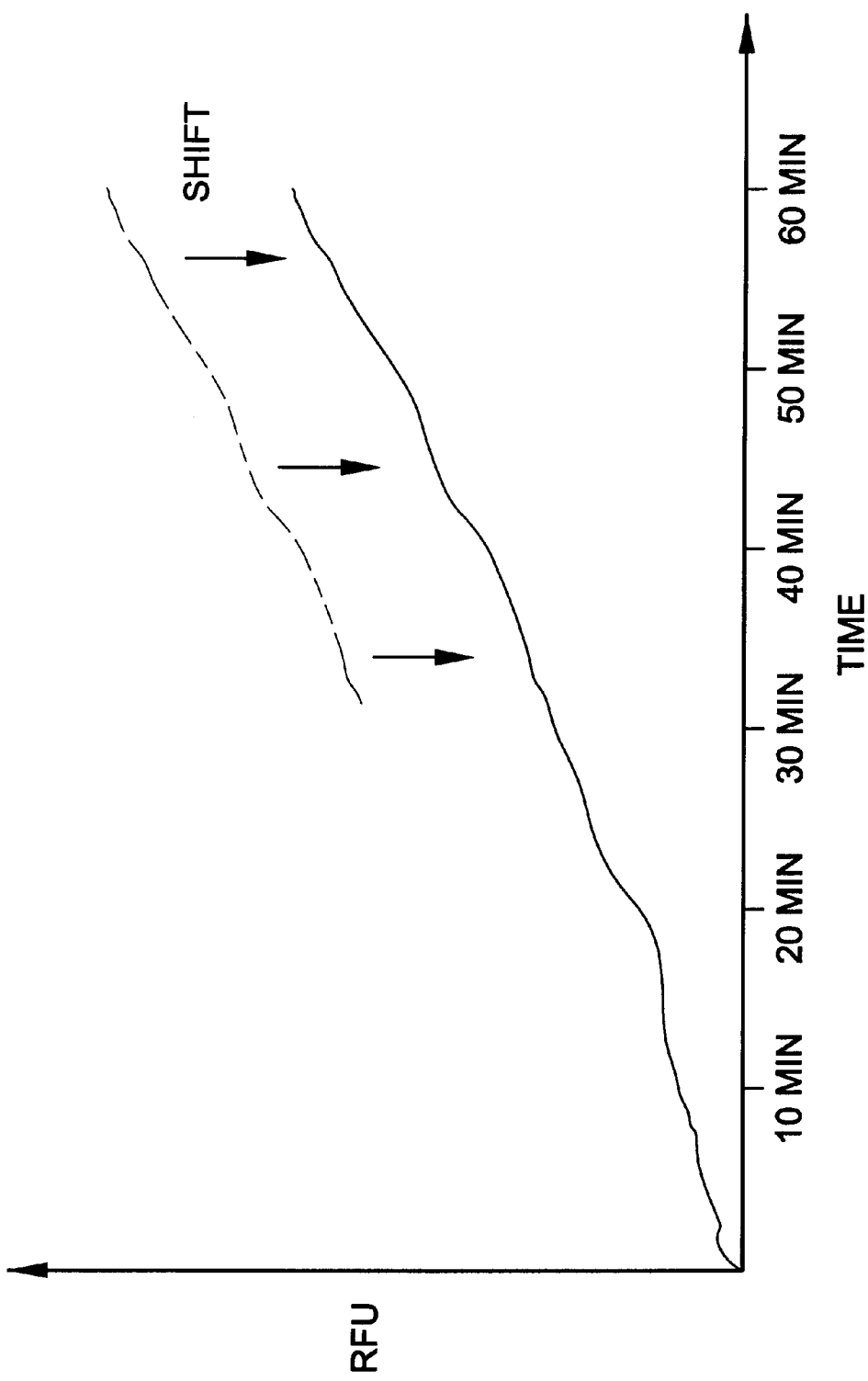
FIG. 13 is a graph which results from performing the step location and removal step of the flowchart show in FIG. 6 on the graph shown in FIG. 11.

The process then continues to step 1450 in which the median value of the difference values $dr_1$ through $dr_{59}$ is determined. Then, in step 1455, the smoothed normalized values occurring after the step are decreased by the difference value calculated for the smoothed normalized value at which the step occurred, and then increased by the median difference value calculated in step 1450. For example, the smoothed normalized values $z_{31}$ through $z_{60}$ are each decreased by the magnitude of difference $dr_{30}$ (the step occurred after the $30^{th}$ reading), and then the smoothed normalized values $z_{31}$ through $z_{60}$ are each increased by the median difference value calculated in step 1450. As shown in FIG. 13, this process has the effect of shifting the entire portion of the curve representing the RFU values of $z_{31}$ through $z_{60}$ downward, thus eliminating the step.

The processing then proceeds to step 1460 where it is determined whether the entire process has been repeated five times. If the value of the count does not equal five, the value of count is increased by one in step in 1465, and the processing returns to step 1410 and repeats as discussed above. However, if the value of the count is equal to five, the processing proceeds to the periodic noise filter step 1500 in the flow chart of FIG. 6.

In the proceeding discussion, it has been assumed that the step being removed is a positive step that results from an abrupt increase in RFU value with time. However, the step removal process will also operate to remove negative steps that occur when the RFU value decreases abruptly over time.

Figure 14:
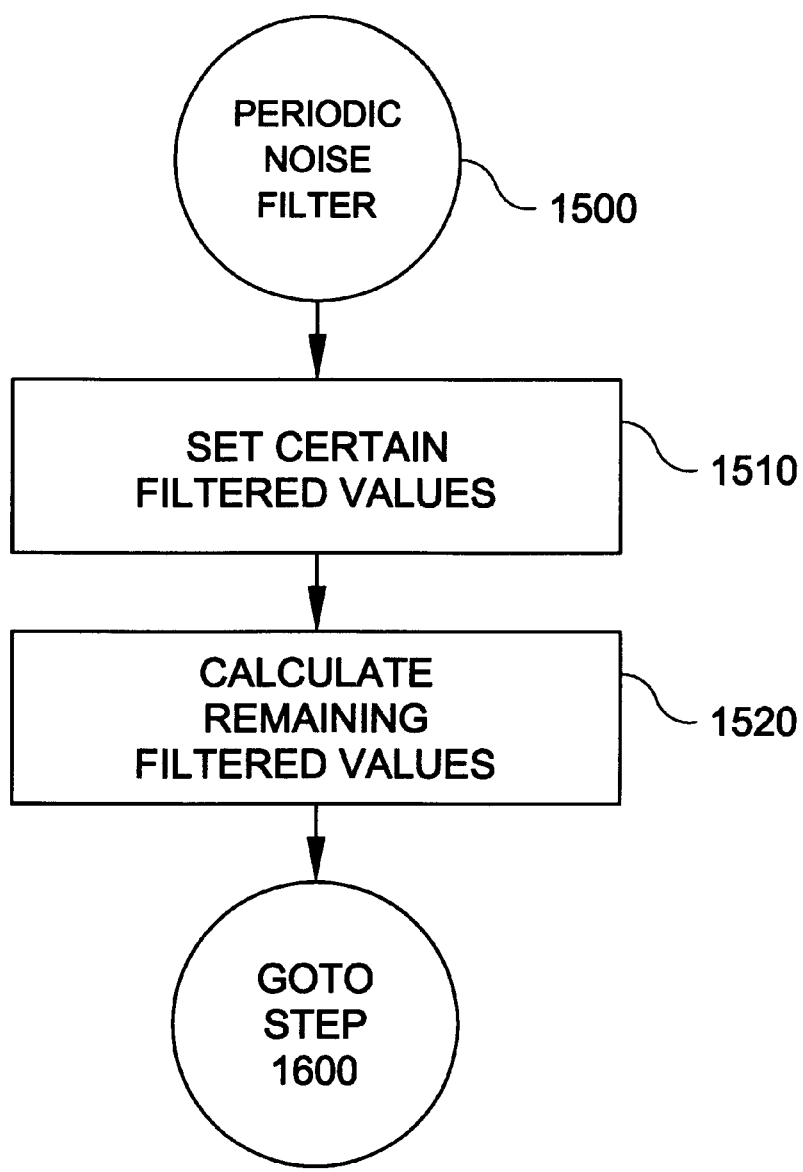
FIG. 14 is a flowchart showing the steps of the periodic noise filter processing step of the flowchart shown in FIG. 6.

The periodic noise filtering operation 1500 is performed to further filter out erroneous values which may exist in the graph shown in FIG. 13 in which the step has been repaired. Details of the periodic noise filtering operation are shown in the flowchart of FIG. 14 and in step 6 of the attached pseudo-code.

Specifically, a five-point moving average is applied to the well reading values $z_1$ through $z_{60}$ represented in the graph of FIG. 13 to provide filtered values $f_1$ through $f_{60}$. In step 1510, the first two filter values $f_1$ and $f_2$ are set equal to the smoothed normalized values $z_1$ and $z_2$, respectively, and the last two filtered values $f_{59}$ and $f_{60}$ are set equal to the two smoothed normalized values $z_{59}$ and $z_{60}$, respectively. Then, in step 1520, the filtered values $f_3$ through $f_{58}$ are determined by taking the average of corresponding smoothed normalized values $z_3$ through $z_{58}$, respectively, and surrounding smoothed normalized values. For example, filtered value $f_3$ is determined by taking the sum of smoothed normalized values $z_1$, $z_2$, $z_3$, $z_4$, and $z_5$, and dividing the sum by 5. Filtered value $f_4$ is determined by taking the sum of smoothed normalized value $z_2$, $z_3$, $z_4$, $z_5$, and $z_6$, and dividing the sum by 5. This process is repeated until all remaining filtered values $f_3$ through $f_{58}$ have been obtained.

The processing then continues to step 1600 shown in FIG. 6, in which the processing determines whether the filtered values $f_1$ through $f_{60}$, which were derived from the above-described steps from the raw well reading values $r_1$ through $r_{60}$, respectively, were actually taken from a well, or, in other words, whether a well was actually present at that location in the microwell array 116 of the sample tray assembly 112. Details of the well-present determination processing are shown in the flowchart in FIG. 15 and in step 7 of the pseudo-code.

Figure 15:
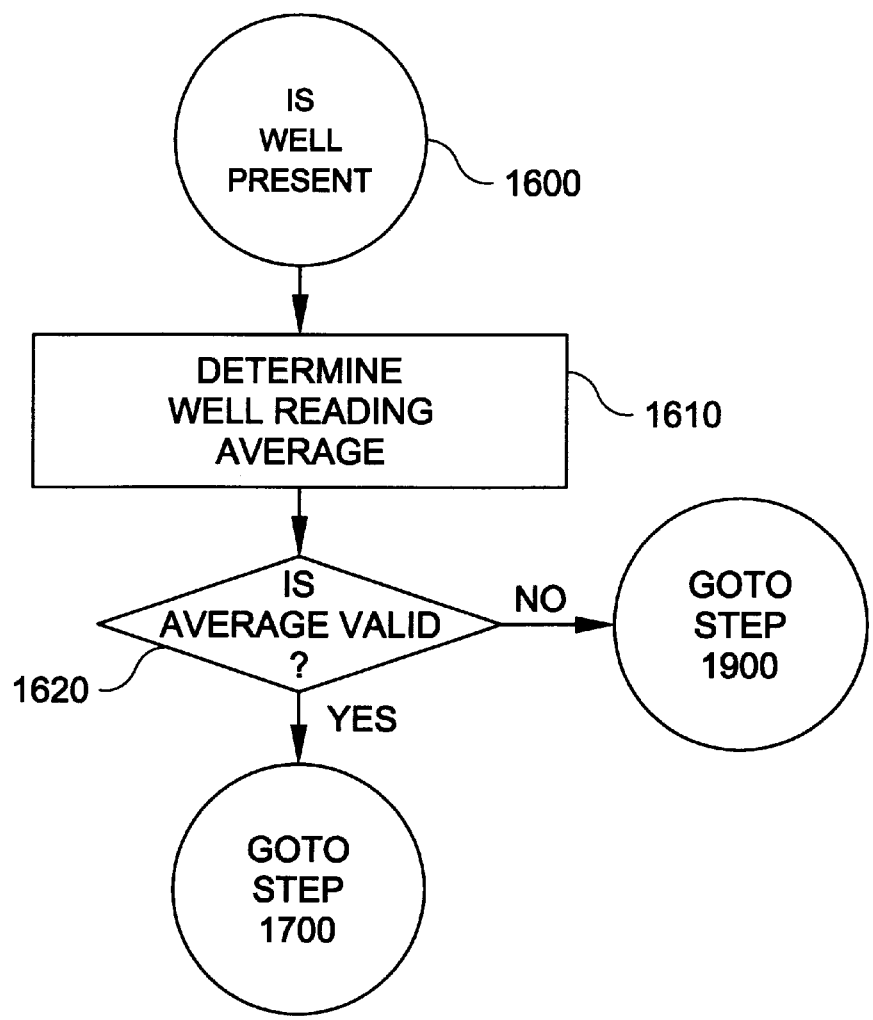
FIG. 15 is a flowchart showing the steps of the well present determining step of the flowchart shown in FIG. 6.

Specifically, in step of 1610 of FIG. 15, a well-present average $wp_{avg}$ is determined by adding the filter values $f_{10}$, $f_{20}$, $f_{30}$, $f_{40}$ and $f_{50}$, and dividing those values by 5. The well-present average $wp_{avg}$ is compared to a well threshold value WP_THRES, which in this example is set to 125.0. If in step 1620, the processing determines that the well-present average $wp_{avg}$ is greater than zero and less than the threshold value WP_THRES, then the processing determines that no well is present and that the data obtained is entirely erroneous. The processing then proceeds to step 1900 in the flowchart shown in FIG. 6, where processing for that well is concluded and an error message is generated. However, if the processing determines in step 1620 that a well is present, the processing continues to step 1700 in the flowchart shown in FIG. 6.

In step 1700 of FIG. 6, the processing establishes a baseline background correction, in which an average value based on the filtered values $f_{15}$ through $f_{20}$ is calculated. The average value is then subtracted from all of the filtered values $f_{21}$ through $f_{60}$. Further details of the background correction operation are shown in the flowchart of FIG. 16 and in step 8 of the pseudo-code.

Figure 16:
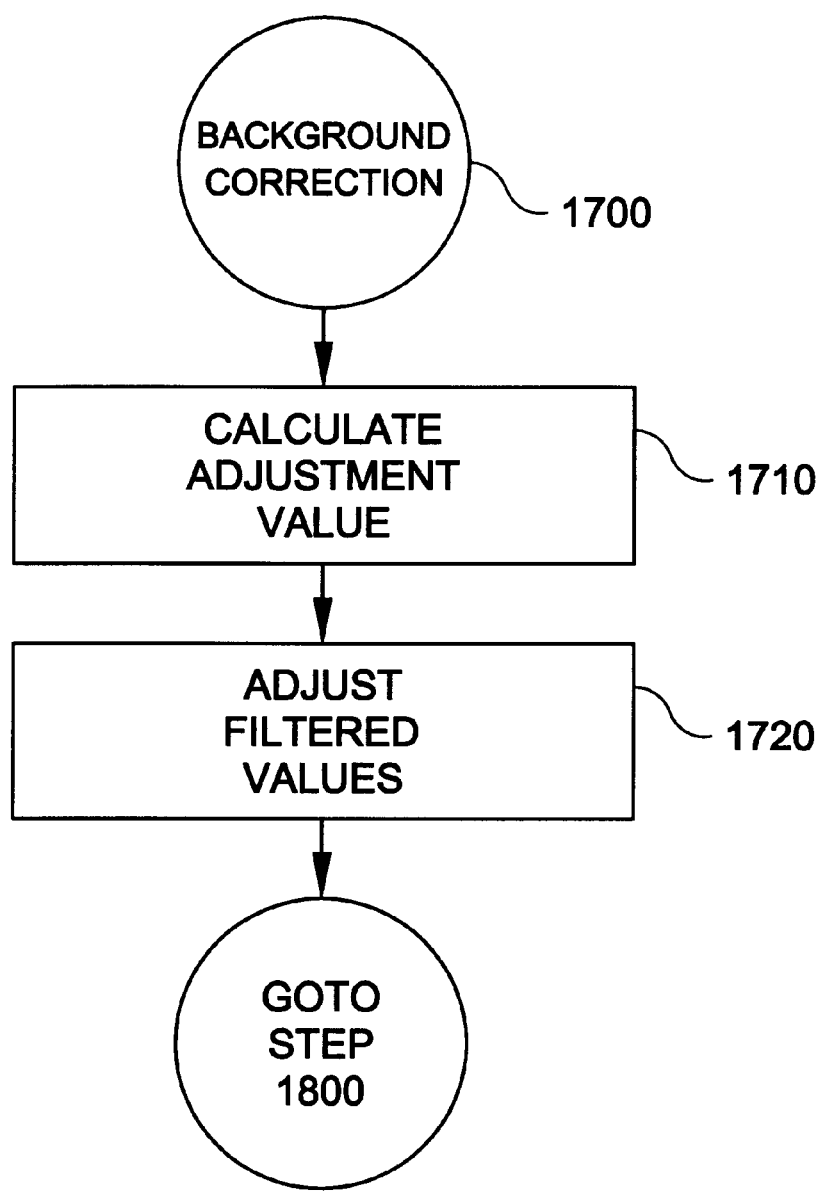
FIG. 16 is a flowchart showing the steps of the background correction step of the flowchart shown in FIG. 6.
Figure 17:
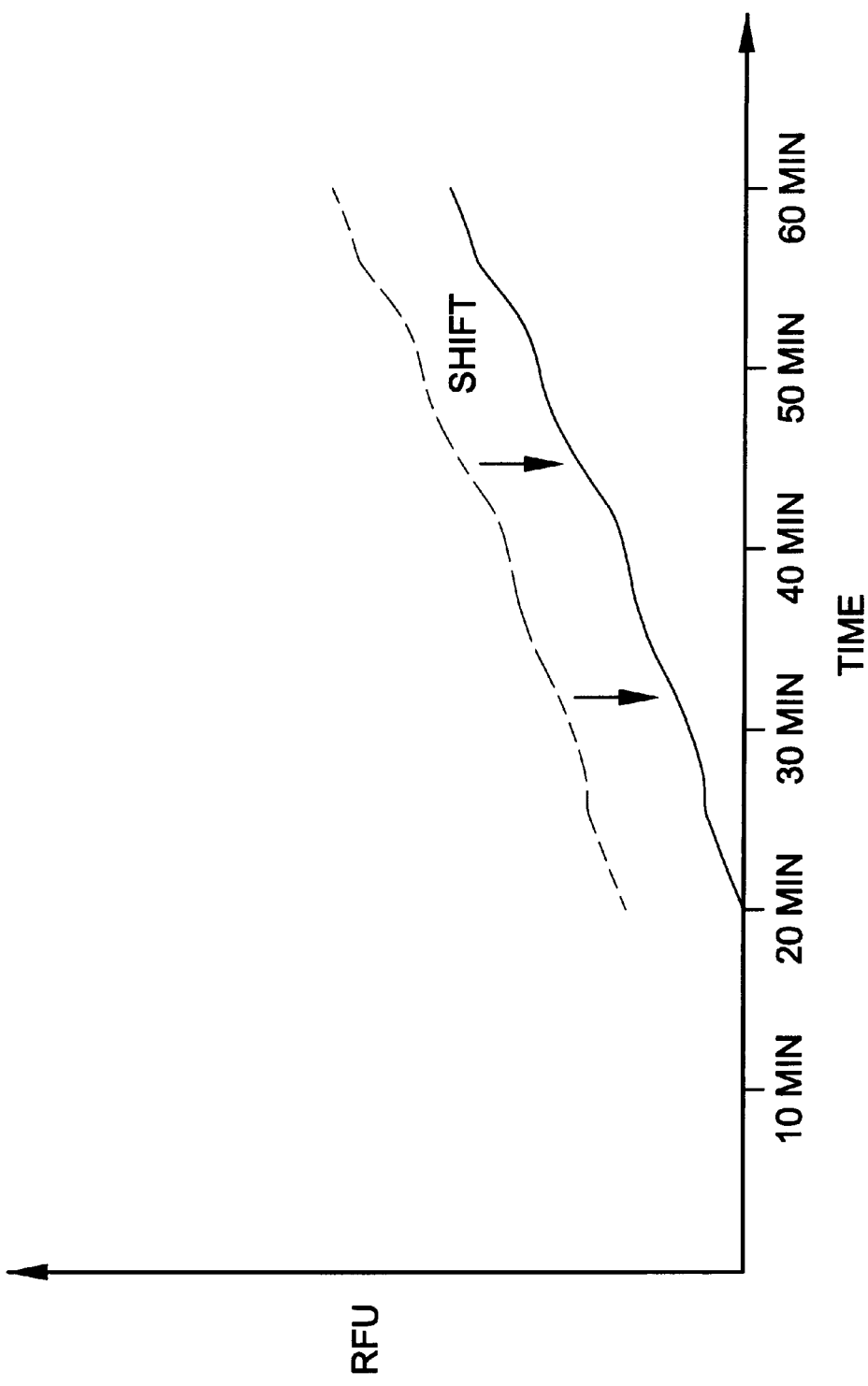
FIG. 17 is a graph which results from performing the background correction step of the flowchart show in FIG. 6 on the graph shown in FIG. 13.

That is, in step 1710 of FIG. 16, the filter values $f_{15}$ through $f_{20}$ are added to produce a sum value. In this example, the sum value is then divided by 6 to provide an initial adjustment value IA. The processing then proceeds to step 1720, in which the initial adjustment value IA is subtracted from each of the filter values $f_{21}$ through $f_{60}$. If, in performing the subtraction, the filter value becomes less than zero, the filtered value is set to zero. As shown in the graph of FIG. 17, this processing shifts the portion of the graph between filter values $f_{21}$ and $f_{60}$ down toward the horizontal axis. The processing then proceeds to the calculated area processing shown in step 1800 in the flowchart of FIG. 6.

Figure 18:
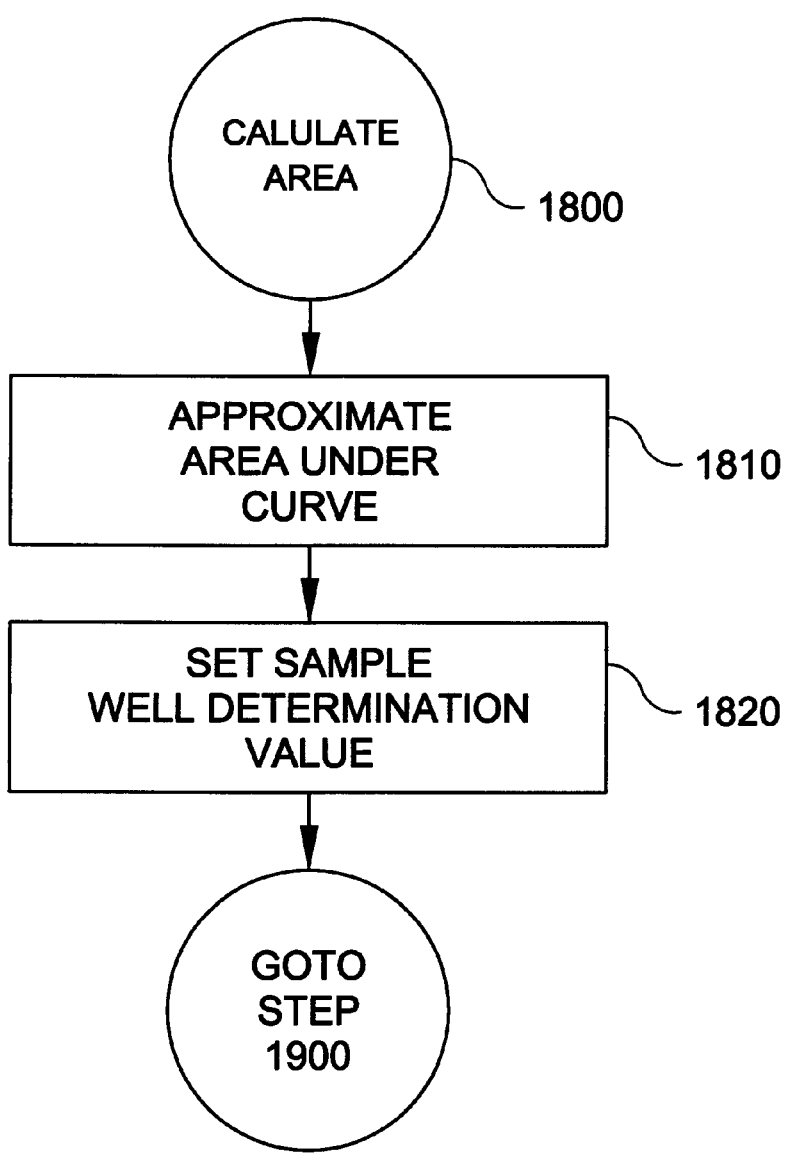
FIG. 18 is a flowchart showing the steps of the area calculation step of the flowchart shown in FIG. 6.

The calculated area processing is described in more detail in the flowchart shown in FIG. 18 and in step 9 of the pseudo-code. Specifically, in step 1810, the area underneath the plot of filtered values $f_{21}$ through $f_{60}$ or in other words, the area between the horizontal axis and the plot of filtered values $f_{21}$ through $f_{60}$ of the graph shown in FIG. 17 is approximated by adding the filtered values $f_{21}$ through $f_{60}$ to arrive at an area value. The sample well determination value sample-value, is set in step 1820, and the processing ends in step 1900 of the flowchart in FIG. 6. Accordingly, the sample-value, that has been obtained is a value that is used to determine whether the sample in the well includes the disease-causing pathogen for which the sample is being tested.

As discussed above, the processing is performed on the first sample microwell which is among the three wells (i.e., first sample microwell, second sample microwell, and third sample microwell) associated with patient sample 1. In this arrangement, first sample microwell includes the reagent to allow for testing of one particular pathogen (e.g., CT), and second sample microwell includes the reagent to allow for testing of another pathogen (e.g., GC). Third sample microwell includes the amplification control AC sample, which, like all the other wells, has been read 60 times.

The processing beginning at step 2000 for determining whether the sample in first sample microwell includes the targeted pathogen is shown in the flowchart of FIG. 19. In particular, in step 2010, the sample-value, which has been obtained by the above processing, is compared to a predetermined upper threshold value. If the magnitude of sample-value$_1$ is greater than the upper threshold value, the processing proceeds to step 2020, where the controller controls the well reading apparatus 100 to provide an indication that the sample in well one has tested positive for the targeted pathogen. This indication can be in the form of a display on the display screen 108, in the form data stored to a disk in the disk drive 106, and/or in the form of data printed out by a printer resident in or attached to the well reading apparatus 100.

However, if the processing determines in step 2010 that the magnitude of sample-value, is not greater than the upper threshold value, the processing proceeds to step 2030 where it is determined whether the magnitude of sample-value$_1$ is greater than a predetermined lower threshold value. If it is determined in step 2030 that the magnitude of sample-value$_1$ is greater than the lower threshold value, the processing proceeds to step 2040 where the well reading apparatus 100 is controlled to indicate that the test results are within the equivocal range. The user can then be given an option to rerun the processing described above with regard to steps 1000–1900, to obtain a new sample-value. The new sample-value$_1$ can then be compared to the upper and lower threshold values as described above. If the results are again equivocal, the well reading apparatus 100 is controlled to indicate that the sample in the microwell is unknown. Patient number 1 can then be contacted to provide another sample, which is then retested in the manner described above.

However, if the processing determines in step 2030 that the magnitude of sample-value$_1$ is not greater than the lower threshold value, the processing proceeds to step 2050. In step 2050, the magnitude of AC-value, is compared to another predetermined threshold value. The AC-value, has been calculated by applying the processing described in steps 1000–1900 to the well readings taken of the AC in the third sample microwell in the sample tray assembly 112, which is associated with the first sample microwell as described above. Under normal conditions, the magnitude of AC-value$_1$ should always be greater than a predetermined upper threshold.

Accordingly, if the processing determines in step 2050 that the magnitude of AC-value$_1$ is greater than the predetermined upper threshold, the processing continues to step 2060 where the well reading apparatus 100 is controlled to indicate that the sample in microwell number 1 is negative, or, in other words, does not include the targeted pathogen (e.g., CT). However, if the processing determines in step 2050 that the magnitude of AC-value$_1$ is not greater than the predetermined upper threshold, the processing proceeds to step 2070, where the well reading apparatus 100 is controlled to indicate that the testing results of the sample in microwell number 1 is indeterminate. The user is then given the option to reprocess the readings taken from microwell 1 in a manner described above with reference to steps 1000–1900 in the flowchart of FIG. 6. If the results of the retest are again found to be equivocal or indeterminate, patient number 1 can be contacted to provide another sample which is then retested in the manner described above.

As discussed above, the manner in which the sample from patient number 1 collected in the second sample microwell is read and analyzed is essentially identical to that described above for the sample in the first sample microwell. Specifically, the 60 readings taken of the sample in the second sample microwell are processed according to steps 1000 through 1900 in FIG. 6 as described above, to produce a sample-value 2. The sample-value$_2$ is then processed in a manner similar to that shown in the flowchart of FIG. 19. However, since microwell number 2 includes a reagent to enable testing for a different pathogen (e.g., GC), the magnitude of sample-value$_2$ is compared to the upper and lower threshold values associated with that particular pathogen. Depending on the results of the comparison, the test results are reported as positive, negative, equivocal or indeterminate.

The above processing can then performed for all of the remaining patient samples in essentially the same manner. As discussed above, if each patient sample is being tested for two pathogens, the microwell array 116 and the sample tray assembly 112 can accommodate samples from a maximum of 30 patients. However, in some instances, the amplification control AC can be included as an internal control present in all of the wells. The amplification control can be illuminated by light of a different frequency emitted by the light emitting/detecting ports 132 of the light sensor bar 130, or by a duplicate light sensor bar (not shown) as described in more detail in the above-referenced copending U.S. patent application Ser. No. 08/929,895. In that event, a set of two microwells for each patient is required to test for two different pathogens (e.g., CT and GC), and only one microwell per patient is required to test for one pathogens (e.g., CT or AC).

It is also noted that before any results are reported to patients, the values obtained from reading the CT, and GC positive and negative control samples are processed in the manner described above with regard to steps 1000 through 1900 of FIG. 6, and the resulting values are analyzed to assure that the known positive and negative control samples have indeed been read as positive and negative samples, respectively. If the readings of any of these control samples are incorrect (i.e., a negative control sample has been identified as a positive sample or vice-versa), all of the sample readings taken for that test type for the entire microwell tray are called into question. All of the sample data is discarded, and the samples can be re-evaluated.

Although only a few exemplary embodiments of the present invention have been described in detail above, those skilled in the art will readily appreciate that many modifications and substitutions are possible in the exemplary embodiments without materially departing from the novel teachings and advantages of the invention. Accordingly, all such modifications and substitutions are intended to be included within the scope of the invention as defined in the following claims.

APPENDIX

```
Pseudo-code
RFU = (r₁ ... r₆₀ ) for one well
NRFU = (n₁ ... n₆₀) for normalizer column
DRFU = (d₁ ... d₆₀) dark for entire plate
  1. Dark Correct Readings
       for i = 1 to 60
           // Dark correct normalizer readings
               cni = ni – di
           // Dark correct well readings
               cri = ri – di
       next i
  2. Smooth Normalizers
       Apply 5 point running median to dark corrected normalizers
           xn₁ = cn₁, xn₂ = cn₂, xn₅₉ = cn₅₉, xn₆₀ = cn₆₀
           for i = 1 to 56
               // Sort cnᵢ, cnᵢ₊₁, cnᵢ₊₂, cnᵢ₊₃, cnᵢ₊₄ and
                  Set xnᵢ₊₂ = cn_midpt
           next i
  3. Dynamic Normalization
         scalar = 3000
         for i = 1 to 60
             nrᵢ = (crᵢ * scalar) / xnᵢ
         next i
  4. Smooth normalized data
       Apply 3 point running median to normalized data
           x₁ = nr₁, x₆₀ = nr₆₀
           for i = 1 to 58
               // Sort nrᵢ, nrᵢ₊₁, nrᵢ₊₂ and Set xᵢ₊₁ = nr_midpt
           next i
```

APPENDIX-continued

```
       Apply 3 point running median to normalized data again
           z₁ = x₁, z₆₀ = x₆₀
           for i = 1 to 58
               // Sort xᵢ, xᵢ₊₁, xᵢ₊₂ and Set zᵢ₊₁ = x_midpt
           next i
  5. Step location and repair
       for count = 1 to 5
         a) Set up differences between adjacent points.
            for i = 1 to 59
                drᵢ = zᵢ₊₁ – Zᵢ
            next i
         b) Calculate average of the differences between points.
            sum = 0
            for i = 1 to 59
                sum = sum + drᵢ
            next i
            'dr = sum / 59
         c) Calculate variance
            sum = 0
            for i = 1 to 59
                sum = sum + (dr₁ – 'dr)²
            next i
            var(dr) = sum / 58        Note: 58
            sum = 0
            for i = 1 to 59
                sum = sum + (drᵢ – 'dr)⁴
            next i
            s = sum
            if var(dr) = 0 then next count
            CRIT_VAL = 4.9
            if s / ( 59 * var(dr)² ) > CRIT_VAL then
                // Step Occurred, Locate where
                max = 0
                for i = 1 to 59
                    // Note: Location method insures
                        finding the 1ˢᵗ maximum
                    // difference
                    if |drᵢ – 'dr| > max then
                        max = |drᵢ – 'dr|
                        maxpt_dr = i
                    'end if
                next i
                Replace max dr point by median difference:
                    Sort dr₁, dr₂, ... dr₅₉ and Set dr_medpt
                // From step point onward, adjust curve down by
                dr_maxpt—dr and then
                // back up by dr_medpt
                for i = (maxpt_dr+1) to 60    Note: maxpt_dr+1
                    zᵢ = zᵢ – dr_maxpt—dr + dr_medpt
                next i
```

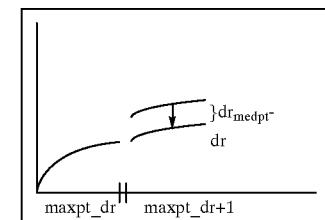

```
            Else
                Break out of count loop
            end if
       next count
  6. Filter
       Apply 5 point moving average to repaired data
           fᵢ = z₁, f₂ = z₂, f₅₉ = z₅₉, f₆₀ = z₆₀
           for i = 1 to 56
               fᵢ₊₂ = (zᵢ + zᵢ₊₁ + zᵢ₊₂ + zᵢ₊₃ + zᵢ₊₄) / 5
           next i
  7. Apply Well Present Threshold (REF. 9)
       wp_avg = (f₁₀ + f₂₀ + f₃₀ + f₄₀ + f₅₀) / 5
       WP_THRES = 125.0
       if wp_avg > 0 and wp_avg < WP_THRES then
           // No well is present
```

APPENDIX-continued

```
        Exit        calculation
    end if
8. Establish baseline
    Average RFU values from K₁ to K₂, where K₂ > K₁
    and are parameters
    currently set to be 15 and 20.
    Initial adjustment
        // Avg points, where K₁ = 15 and K₂ = 20
        sum = 0
        for i = K₁ to K₂
            sum = sum + f_i
        next i
        IA = sum / (K₂ - K₁ + 1)
        // No need to baseline points 1 thru 20, they
        // are not used in the area.
        for i = (K₂ + 1) to 60        // 21 to 60
            fi = fi - IA
            if f_i < 0 then f_i = 0
        next i
9. Calculate Area starting at (K₂ + 1) point (21ˢᵗ)
    Area = f21 + f22 + . . . + f59 + f60
    area = 0
    for i = (K₂ + 1) to 60        // 21 to 60
        area = area + f_i
    next i
```

What is claimed is:

1. A computerized method for controlling a system to analyze numerical data pertaining to a sample assay performed on at least one biological or chemical sample, said numerical data including a set of data pertaining to said sample, said set of data including a plurality of data values, each representing a condition of said sample read at a respective time, said method comprising the steps of:

for each said set of data, performing the steps of:
  assigning a respective numerical value to each of said data values;
  mathematically combining at least some of said numerical values to generate a total value;
  comparing said total value to a threshold value; and
  controlling said system to indicate whether said sample has a predetermined characteristic based on a result of said total value comparing step.

2. A method as claimed in claim 1, wherein said assigning step comprises the steps of:
  arranging said data values in a sequence representative of said respective times;
  comparing at least some of said data values in said sequence to other of said data values; and
  assigning said respective numerical values to said data values based on a result of said data value comparing step.

3. A method as claimed in claim 1, wherein said assigning step comprises the steps of:
  arranging said data values in a sequence representative of said respective times;
  comparing the magnitude of each of said data values in said sequence to the magnitude of an adjacent data value in said sequence to determine whether a difference between the magnitude of said data value and of said adjacent data value is greater than a predetermined amount, and if said magnitude is greater said predetermined amount, identifying said data value as a step data value; and
  adjusting the magnitude of each of said data values subsequent to said step data value in said sequence by an adjustment amount which is based on said magnitude to produce said respective numerical values assigned to said subsequent data values.

4. A method as claimed in claim 1, further comprising the steps of:
  for said each set of data, further performing the steps of:
    averaging at least some of said numerical values to generate an average value;
    comparing said average value to an average threshold value to determine whether an erroneous condition in said set of data exists; and
    if said erroneous condition is determined to exist, deleting said mathematically combining, total value comparing, and controlling steps, and controlling said system to generate an error indication.

5. A method as claimed in claim 1, wherein said assigning step comprises the steps of:
  generating an average value based on at least some of said numerical values; and
  adjusting the magnitude of at least some of said data values based on said average value to produce said numerical values assigned to said data values.

6. A method as claimed in claim 1, wherein said mathematically combining step adds said numerical values to generate said total value.

7. A method as claimed in claim 1, wherein:
  said sample assay comprising a plurality of said samples, and said numerical data includes a plurality of sets of data, each of which pertains to a respective one of said samples; and
  said method performs said assigning, mathematically combining, total value comparing and controlling steps for each of said plurality of data sets.

8. A computerized method for controlling a system to analyze numerical data pertaining to a sample assay performed on at least one biological or chemical sample, said numerical data including a set of data pertaining to said sample, said set of data including a plurality of data values, each representing a condition of said sample read at a respective time, said method comprising the steps of:

for each said set of data, performing the steps of:
  representing each of said plurality of data values as a point on a graph having a vertical axis representing the magnitude of said value and a horizontal axis representing a period of time during which readings of said sample were taken to obtain said plurality of data values;
  identifying points on said graph having an anomalous characteristic, and correcting said anomalous points to produce a corrected plot of points on said graph, each of said points of said corrected plot of points representing a magnitude of a corresponding one of said values;
  calculating an area value representing an approximate area between at least a portion of said corrected plot of points on said graph and said horizontal axis; and
  comparing said area value to a threshold value to determine whether a certain condition exists in said sample to which said set of data pertains.

9. A method as claimed in claim 8, wherein:
  said identifying and correcting step identifies a step characteristic in said plot of points, and eliminates said step characteristic when producing said corrected plot of points on said graph.

10. A method as claimed in claim 8, wherein for each said set of data, said method further comprises the steps of:
  prior to performing said area calculating step, calculating a correction value based on at least some of said data values; and shifting said portion of said corrected plot of points on said graph with respect to said horizontal axis.

11. A method as claimed in claim 8, wherein for each said set of data, said method further comprises the steps of:
   obtaining an average value representing an average of the magnitudes of at least some of said points of said corrected plot of points;
   comparing said average value to an error indication threshold to determine whether an error condition exists in relation to said set of data; and
   if said error condition is determined to exist, deleting said area value calculating and comparing steps.

12. A computer readable medium of instructions for controlling a system to analyze numerical data pertaining to a sample assay performed on at least one biological or chemical sample, said numerical data including a set of data pertaining to said sample, said set of data including a plurality of data values, each representing a condition of said sample read at a respective time, said medium of instructions comprising:
   a first group of instructions for controlling said system to assign a respective numerical value to each of said data values;
   a second group of instructions for controlling said system to mathematically combine at least some of said numerical values to generate a total value;
   a third group of instructions for controlling said system to compare said total value to a threshold value; and
   a fourth group of instructions for controlling said system to indicate whether said sample has a predetermined characteristic based on a result of said comparison of said total value and said threshold value.

13. A computer readable medium of instructions as claimed in claim 12, wherein said first group of instructions comprises:
   a fifth group of instructions for controlling said system to arrange said data values in a sequence representative of said respective times;
   a sixth group of instructions for controlling said system to compare at least some of said data values in said sequence to others of said data values; and
   a seventh group of instructions for controlling said system to assign said respective numerical values to said data values based on a result of said comparison of said data values to said other data values.

14. A computer readable medium of instructions as claimed in claim 12, wherein said first group of instructions comprises:
   an eighth group of instructions for controlling said system to arrange said data values in a sequence representative of said respective times;
   a ninth group of instructions for controlling said system to compare the magnitude of each of said data values in said sequence to the magnitude of an adjacent said data value in said sequence to determine whether a difference between the magnitude of said data value and said adjacent data value is greater than a predetermined amount, and if said magnitude is greater than said predetermined amount, identifying said data value as a step data value; and
   a tenth group of instructions for controlling said system to adjust the magnitude of each of said data values subsequent to said step data value in said sequence by an adjustment amount which is based on said magnitude to produce said respective numerical values assigned to said subsequent data values.

15. A computer readable medium of instructions as claimed in claim 12, further comprising:
   an eleventh group of instructions for controlling said system to average at least some of said numerical values to generate an average value;
   a twelfth group of instructions for controlling said system to compare said average value to an average threshold value to determine whether an anomalous condition in said set of data exists; and
   a thirteenth group of instructions for controlling said system to delete said mathematically combining, first comparing, and controlling steps, and for controlling said system to generate an error indication, if said erroneous condition is determined to exist.

16. A computer readable medium of instructions as claimed in claim 12, wherein said first group of instructions comprises:
   a fourteenth group of instructions for controlling said system to generate an average value based on at least some of said numerical values; and
   a fifteenth group of instructions for controlling said system to reduce the magnitude of at least some of said data values by a reduction amount which is based on said average value to produce said numerical values assigned to said data values.

17. A computer readable medium of instructions as claimed in claim 12, wherein said second group of instructions controls said system to add said numerical values to generate said total value.

18. A computer readable medium of instructions as claimed in claim 12, wherein:
   said sample assay comprises a plurality of said samples, and said numerical data includes a plurality of sets of data, each of which pertains to a respective said sample; and
   said first, second, third and fourth groups of instructions control said system to perform said assigning, mathematically combining, first comparing and controlling steps for each of said plurality of data sets.

* * * * *